(12) United States Patent
Traut et al.

(10) Patent No.: US 7,120,954 B2
(45) Date of Patent: Oct. 17, 2006

(54) HEAD IMMOBILIZER

(75) Inventors: James Traut, Poughkeepsie, NY (US); Sean Phillips, Chicago, IL (US)

(73) Assignee: Laerdal Medical Corporation, Wappinger Falls, NY (US)

( * ) Notice: Subject to any disclaimer, the term of this patent is extended or adjusted under 35 U.S.C. 154(b) by 0 days.

(21) Appl. No.: 10/622,059

(22) Filed: Jul. 18, 2003

(65) Prior Publication Data
US 2004/0016057 A1   Jan. 29, 2004

Related U.S. Application Data

(63) Continuation-in-part of application No. 09/741,296, filed on Dec. 19, 2000, now Pat. No. 6,637,057.

(51) Int. Cl.
  *A61G 1/04*    (2006.01)
  *A61F 5/37*    (2006.01)
(52) U.S. Cl. .................................. 5/637; 5/628; 5/622
(58) Field of Classification Search ............... 5/637, 5/636, 640, 643, 625, 627, 628, 621, 622; 128/870, 869
See application file for complete search history.

(56) References Cited

U.S. PATENT DOCUMENTS

| | | | | |
|---|---|---|---|---|
| 3,651,734 A | * | 3/1972 | McSherry | 411/15 |
| 3,737,923 A | * | 6/1973 | Prolo | 5/628 |
| 3,897,777 A | * | 8/1975 | Morrison | 5/622 |
| 3,957,262 A | * | 5/1976 | McReynolds | 5/637 |
| 4,034,748 A | * | 7/1977 | Winner | 602/19 |
| 4,058,112 A | * | 11/1977 | Johnson | 5/651 |
| 4,182,322 A | * | 1/1980 | Miller | 5/637 |
| 4,252,113 A | * | 2/1981 | Scire | 5/628 |
| 4,259,757 A | * | 4/1981 | Watson | 5/637 |
| 4,297,994 A | * | 11/1981 | Bashaw | 5/637 |
| 4,400,820 A | * | 8/1983 | O'Dell et al. | 378/209 |
| 4,528,981 A | * | 7/1985 | Behar | 5/637 |
| 4,571,757 A | * | 2/1986 | Zolecki | 5/628 |
| 4,640,275 A | * | 2/1987 | Buzzese et al. | 5/622 |
| 4,771,493 A | * | 9/1988 | Park | 5/637 |
| 4,794,656 A | * | 1/1989 | Henley, Jr. | 5/628 |
| 4,905,712 A | * | 3/1990 | Bowlin et al. | 5/637 |
| 4,928,711 A | * | 5/1990 | Williams | 5/628 |
| 4,964,418 A | * | 10/1990 | Wilson | 128/857 |
| 4,979,520 A | * | 12/1990 | Boone et al. | 128/870 |

(Continued)

*Primary Examiner*—Robert G. Santos
(74) *Attorney, Agent, or Firm*—Frommer Lawrence & Haug LLP

(57) ABSTRACT

A base headboard for supporting the back of an injured person's head has an elongated slot with teeth racks disposed on either side of the injured person's head. The headboard also comprises straps for attaching to a spine board. Two side head blocks are removably attached to the headboard using plunger-type locks that engage an elongated slot on each side of a center portion of the headboard. Each lock is engaged to a slot of the headboard through a separate elongated slot in the corresponding head block. Advantageously, a head block may be adjusted by moving the engagement of the lock along each independent slot in the headboard and head block, respectively. In addition, a head block may be rotated around its lock. Head pads and straps, and pads and straps for cervical collars that come into contact with a patient may be replaceable and packaged in a kit, thereby allowing the durable components (such as head blocks and headboard) to be reused indefinitely and reducing cleaning costs and minimizing exposure to pathogens. Such a kit of replaceable parts may also reduce material waste compared having all disposable components without any durable components (i.e. head immobilizers).

26 Claims, 24 Drawing Sheets

U.S. PATENT DOCUMENTS

| | | | |
|---|---|---|---|
| 5,211,185 A * | 5/1993 | Garth et al. | 5/628 |
| 5,236,153 A * | 8/1993 | LaConte | 244/118.6 |
| 5,265,625 A * | 11/1993 | Bodman | 5/637 |
| 5,305,754 A * | 4/1994 | Honeywell et al. | 5/626 |
| 5,360,393 A * | 11/1994 | Garth et al. | 602/17 |
| 5,400,802 A * | 3/1995 | Niemeyer et al. | 5/637 |
| 5,657,766 A * | 8/1997 | Durham | 5/637 |
| D384,155 S * | 9/1997 | Crist | D24/191 |
| 5,944,016 A * | 8/1999 | Ferko, III | 128/869 |
| 6,170,486 B1 * | 1/2001 | Islava | 128/869 |
| 6,176,549 B1 * | 1/2001 | Karash | 297/391 |
| 6,230,712 B1 * | 5/2001 | Køhnke | 128/869 |
| 6,244,270 B1 * | 6/2001 | Lutian et al. | 128/869 |
| 6,367,200 B1 * | 4/2002 | LaConte | 49/465 |
| 6,435,188 B1 * | 8/2002 | Tyrrell | 128/870 |
| D479,878 S * | 9/2003 | Phillips et al. | D24/191 |
| 6,622,324 B1 * | 9/2003 | VanSteenburg et al. | 5/621 |
| 6,637,057 B1 * | 10/2003 | Phillips et al. | 5/637 |
| 6,820,621 B1 * | 11/2004 | DeMayo | 128/845 |
| 6,934,987 B1 * | 8/2005 | Newkirk et al. | 5/613 |
| 6,941,951 B1 * | 9/2005 | Hubert et al. | 128/845 |
| 2002/0073487 A1 * | 6/2002 | Phillips et al. | 5/628 |
| 2003/0159216 A1 * | 8/2003 | Tomcany et al. | 5/628 |
| 2003/0167569 A1 * | 9/2003 | Newkirk et al. | 5/613 |
| 2004/0016057 A1 * | 1/2004 | Traut et al. | 5/628 |
| 2004/0049852 A1 * | 3/2004 | Phillips et al. | 5/626 |
| 2004/0123389 A1 * | 7/2004 | Boucher et al. | 5/623 |
| 2005/0229313 A1 * | 10/2005 | Tomcany et al. | 5/628 |
| 2005/0241068 A1 * | 11/2005 | Tomcany et al. | 5/622 |

* cited by examiner

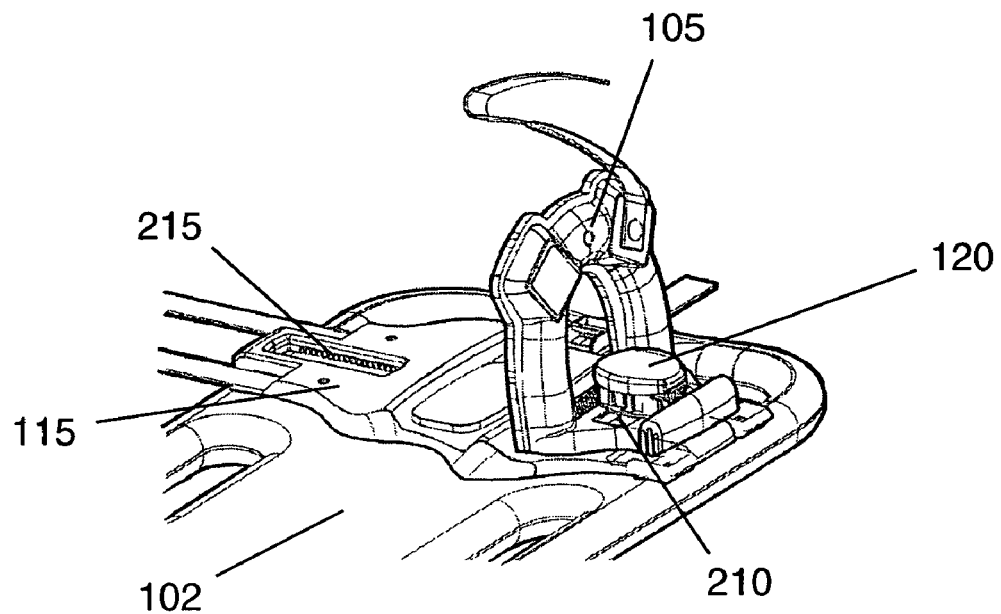
FIGURE 2B
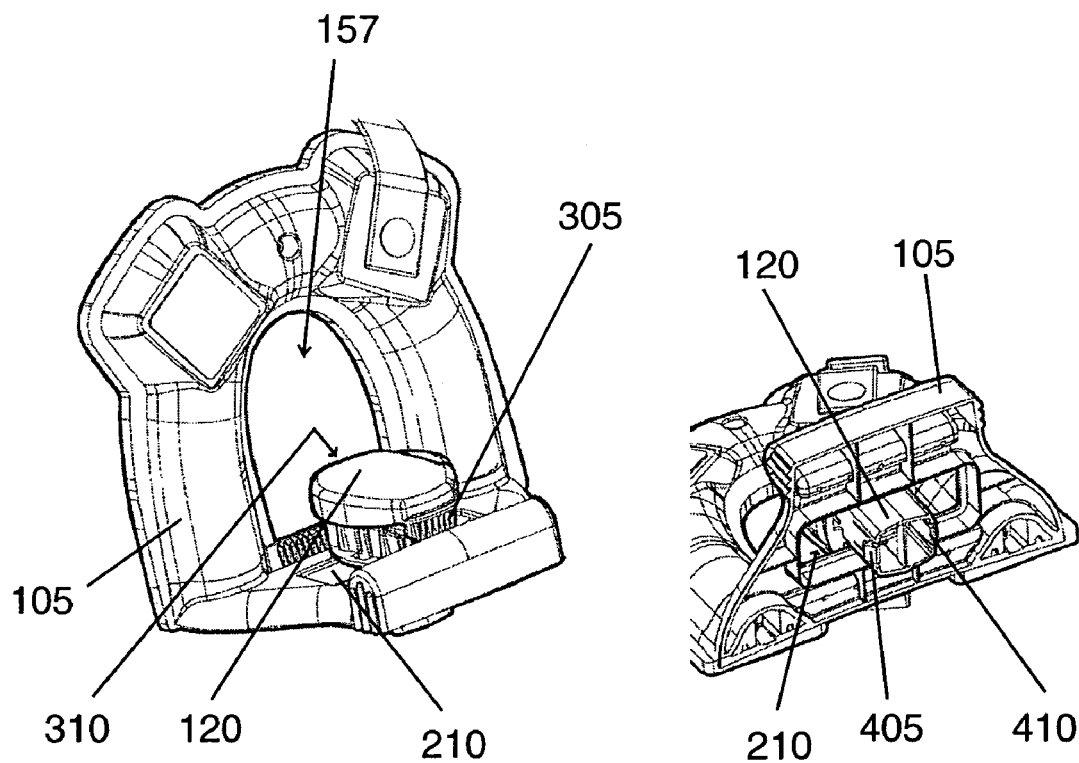
FIGURE 3  FIGURE 4A

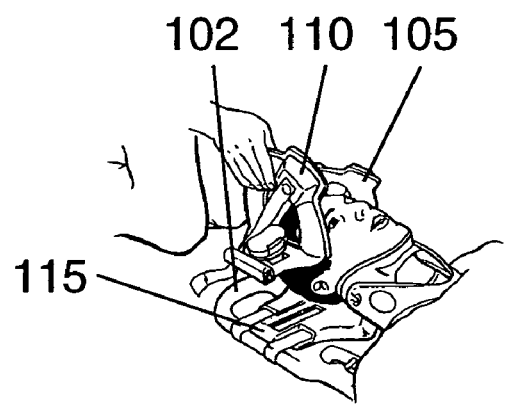
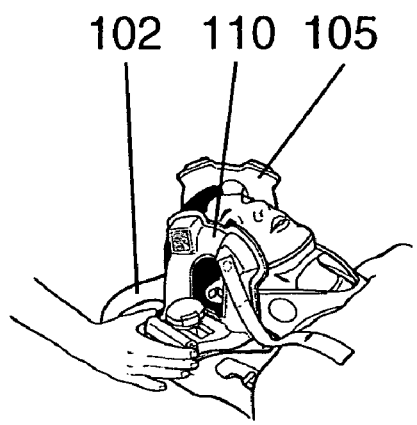
FIGURE 8        FIGURE 9
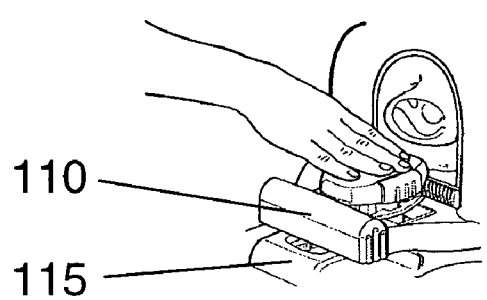
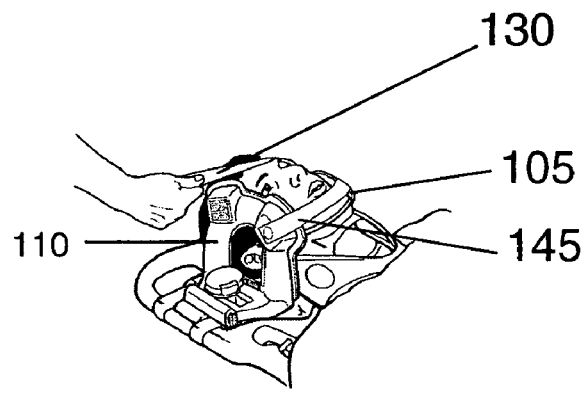
FIGURE 10        FIGURE 11

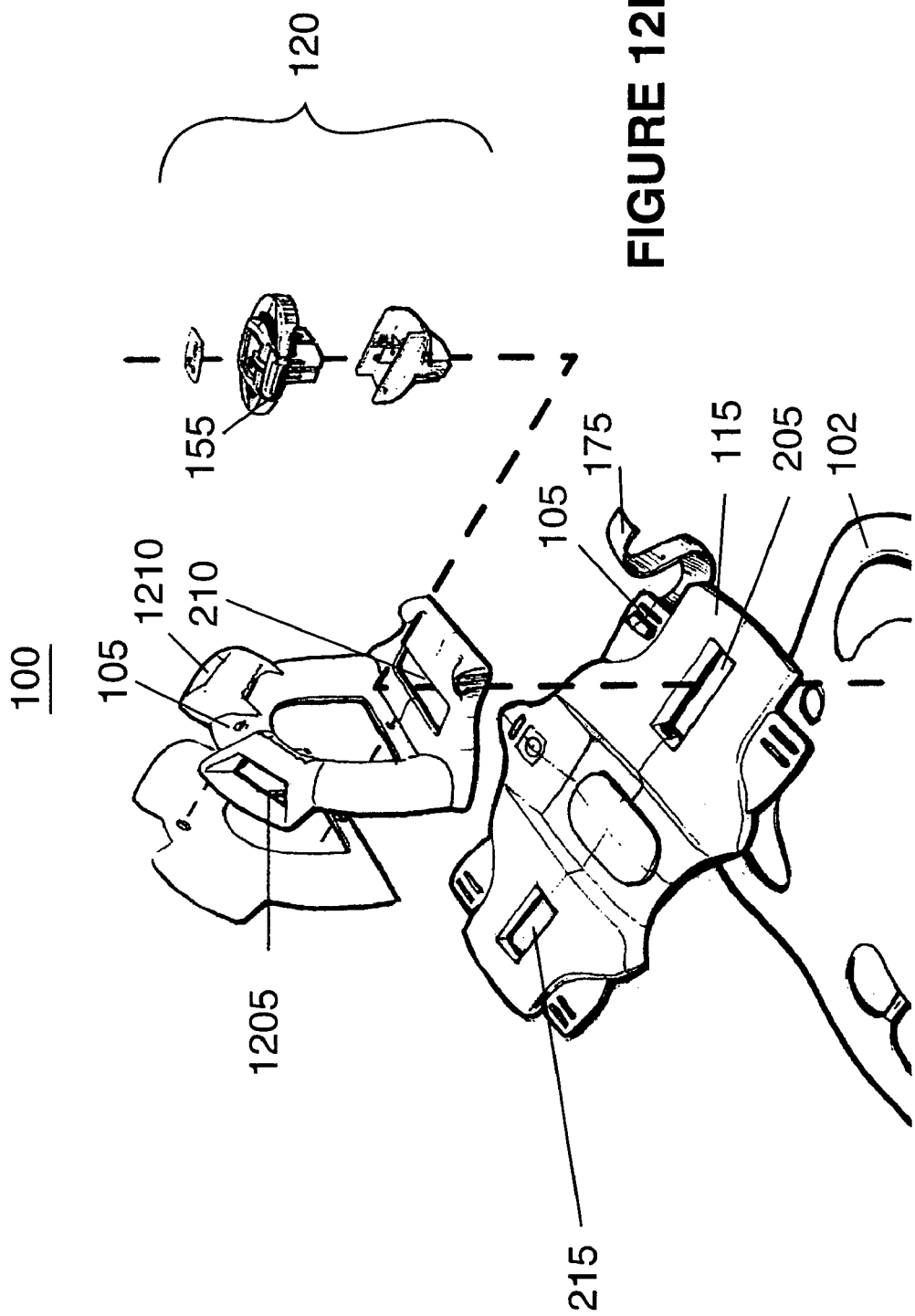

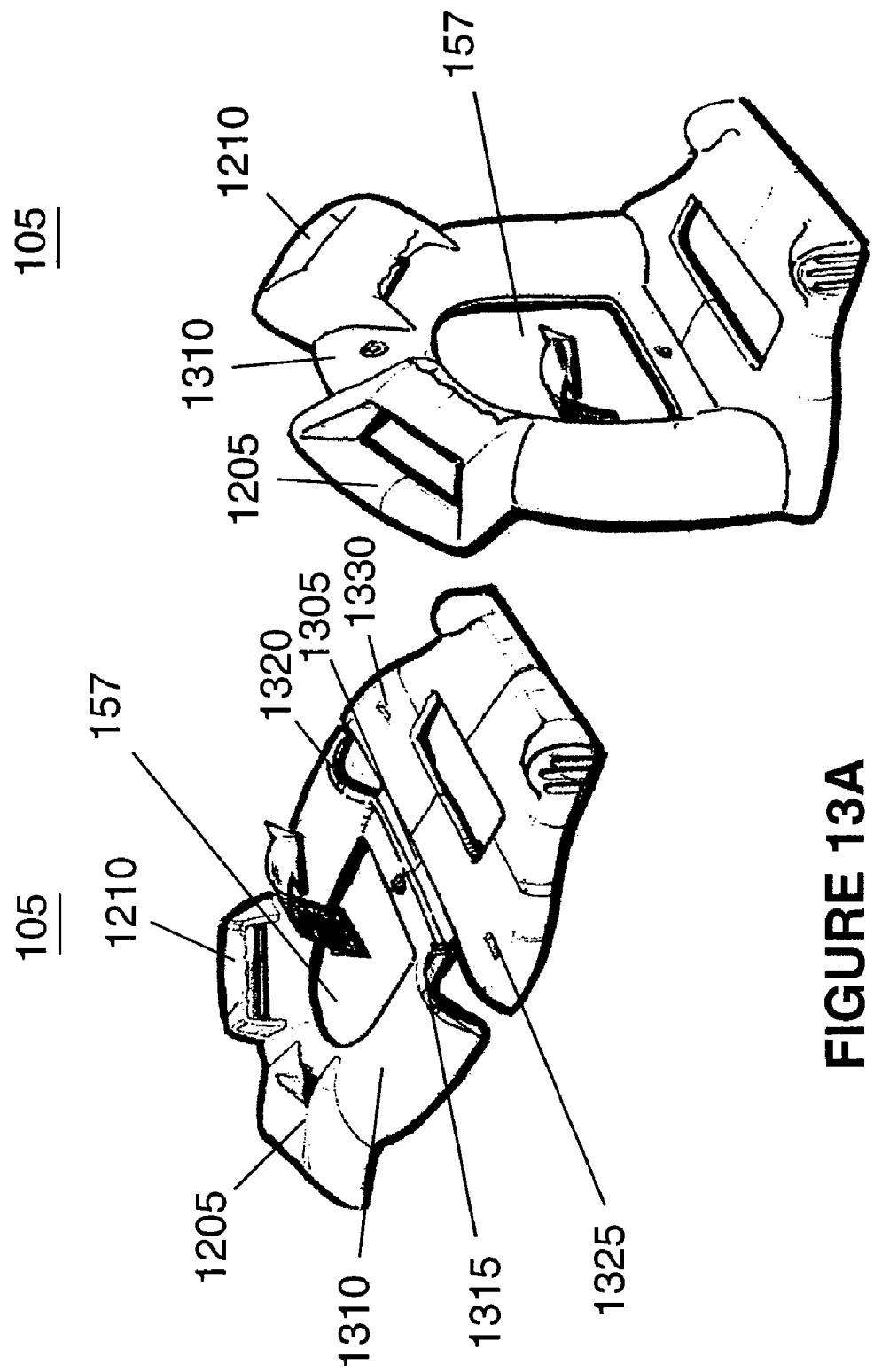

FIGURE 18A
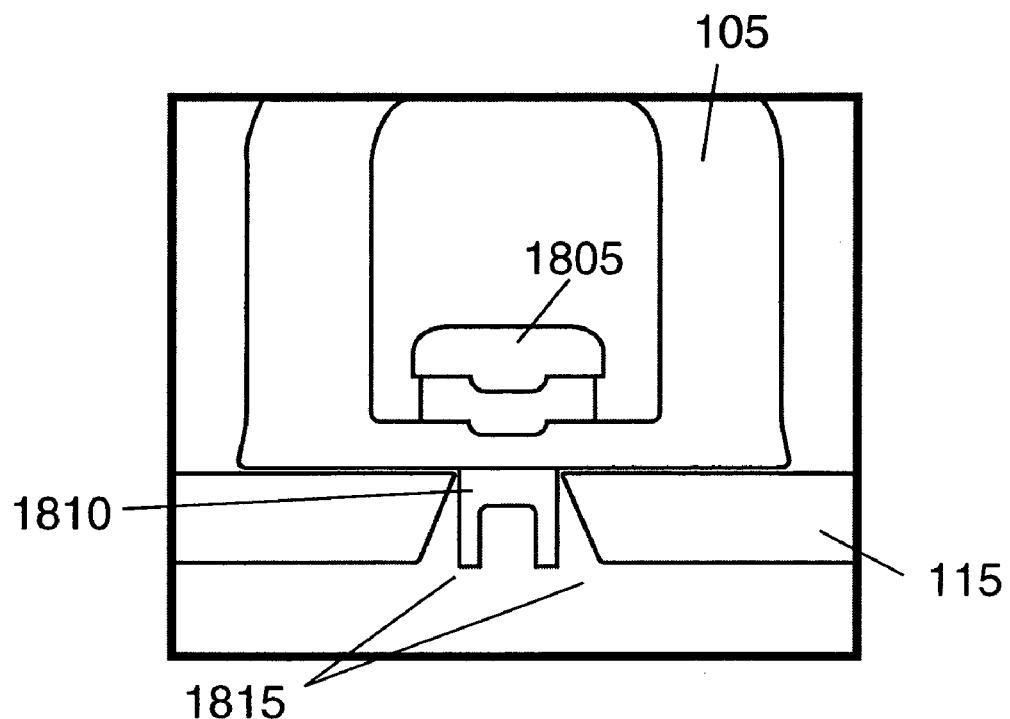
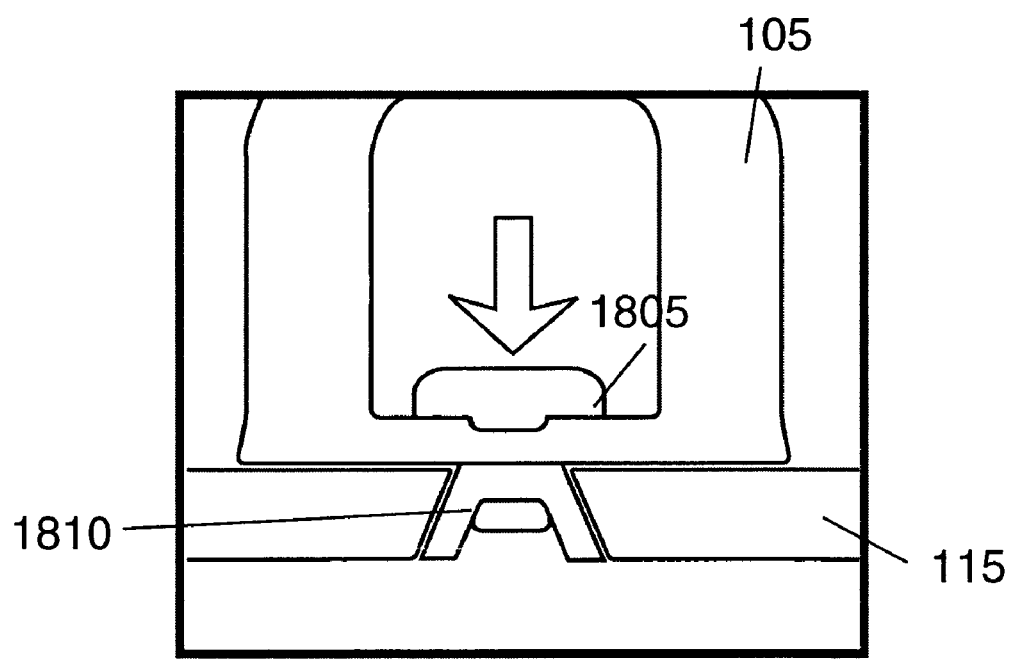
FIGURE 18B

| X-Ray View Point | Structural Feature | Resulting X-Ray Image |
|---|---|---|
|  |  U-channel section |  |
| 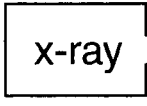 |  Ribbing | 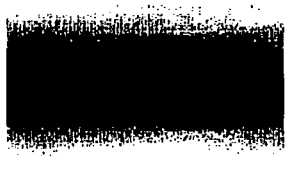 |
| 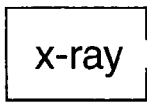 |  Curvilinear with Tapered/ Feathered Ends | 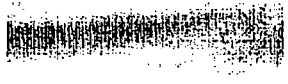 |
FIGURE 19A

Bell Shape
Cross-Section

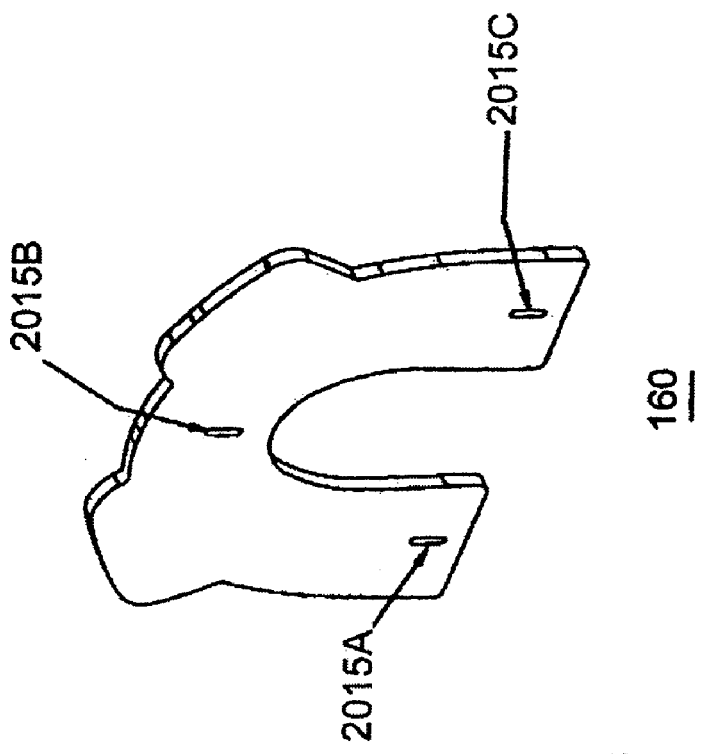
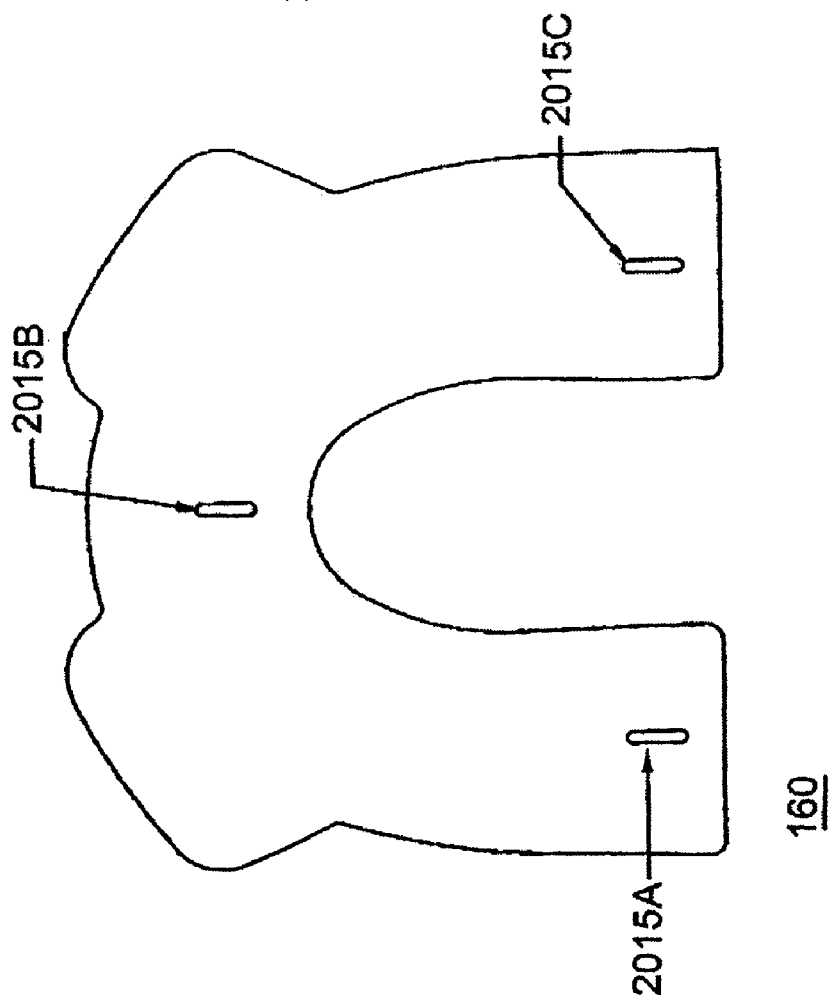

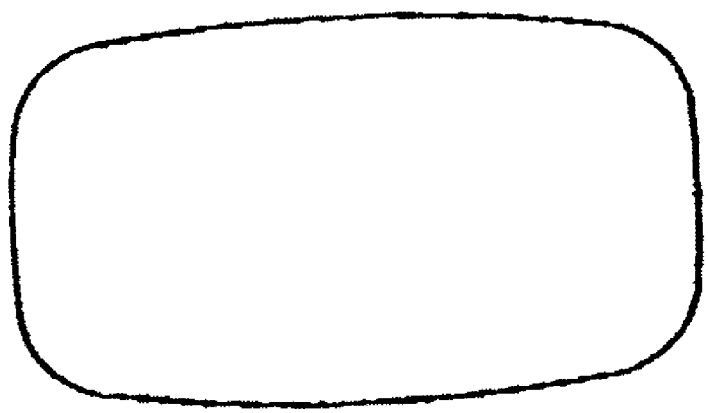

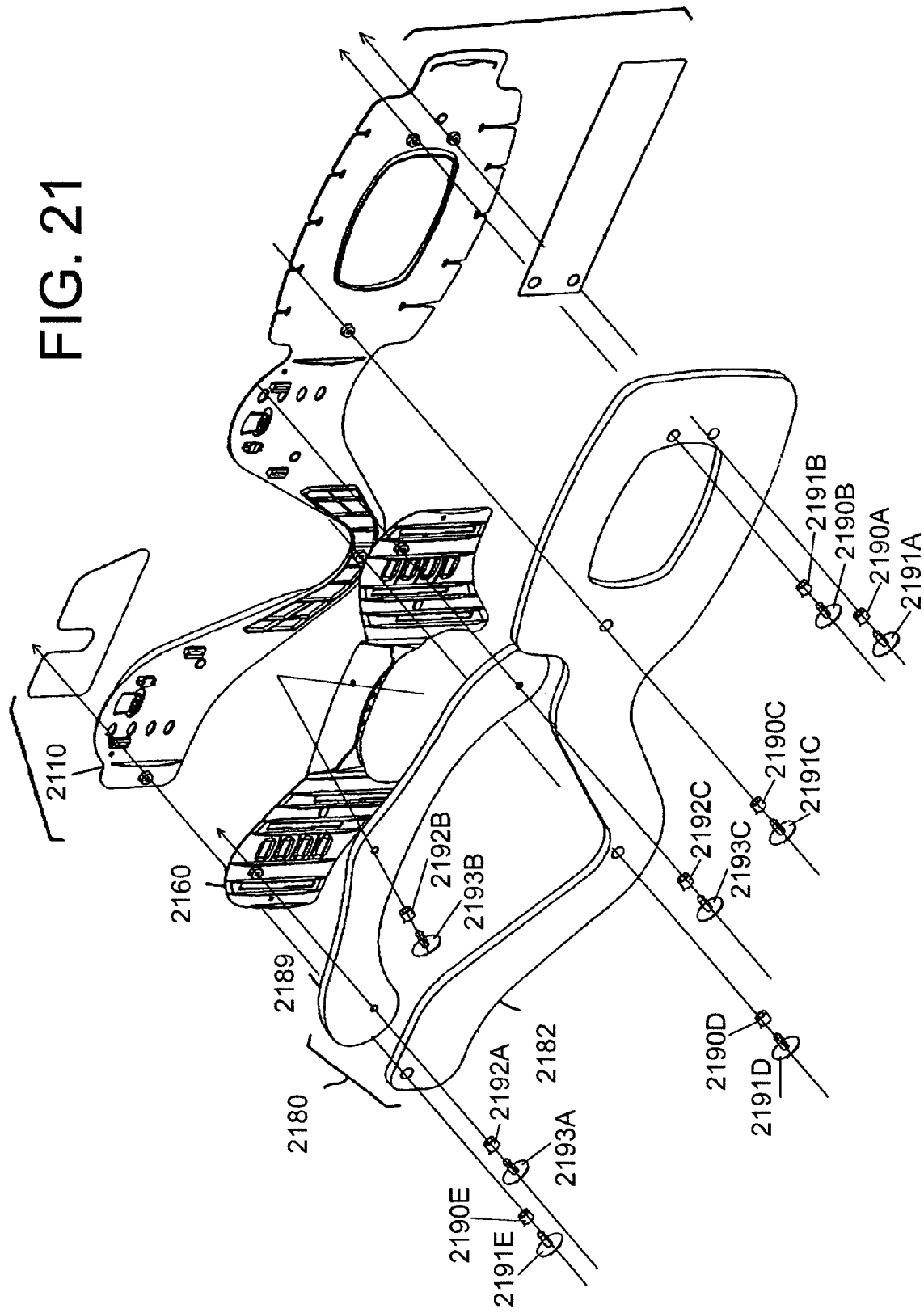

HEAD IMMOBILIZER

CROSS REFERENCE TO RELATED APPLICATIONS

This application is a continuation-in-part application to U.S. patent application Ser. No. 09/741,297, filed Dec. 19, 2000, now U.S. Pat. No. 6,637,057.

FIELD OF THE INVENTION

The present invention relates generally to an improved head immobilization apparatus that is attachable to, and detachable from, a spine board of the type employed by emergency medical personnel for transporting injured persons.

BACKGROUND OF THE INVENTION

Spine boards have been used by physicians and emergency medical personnel for a number of years in the transport of injured or incapacitated persons. Particular care and attention is needed for the immobilization of the head and neck of an injured person being transported. Head and cervical spine immobilization is necessary to prevent possible neck (cervical spine) injuries from being exacerbated during transport. It is desirable that such immobilization be performed quickly and properly after an injured person has otherwise been properly secured on a spine board. Thus, a head immobilization apparatus should provide a high level of motion restriction with an intuitive design allowing for simple and proper application. The apparatus should be fully adjustable to fit the injured person. Given the limited space in an ambulance, the apparatus should also be compact for easy storage.

After the injured person has been properly immobilized for transport, emergency medical personnel should have good visual and tactile access to the eyes, ears, mouth, nose, and neck of the injured person to properly diagnose the nature and extent of the injuries. Hence, a head immobilization apparatus should provide such access to the injured person. The injured person may need to be x-rayed while still on a spine board. Thus, the head immobilizer should have a high level of x-ray transparency.

With respect to head immobilization apparatuses, reference is made to the following:

Bodman, U.S. Pat. No. 5,265,625, relates to a device for immobilizing the head to prevent further injuries, such as neck injuries, including left and right complimentary blocks. Each block has a skull-supporting surface. The blocks contact the skull with the skull supporting surfaces diverging outwardly and upwardly to provide a wedging action to immobilize the skull against left and right movement as well as to position the height of the skull so that alignment of the neck is achieved. The skull-supporting surface surrounds but does not cover the ear so that assessment may be made easily. The left and right blocks may be disposable for one time use or permanently mounted on a carrier for reuse.

McReynolds et al, U.S. Pat. No. 5,207,716, relates to an apparatus for supporting and immobilizing a head during surgery or examination by a treating physician. A headrest is secured to a base support. The headrest has open sides and is shaped to engage a patient's head. A pair of immobilizing jaws engages the head from the side to hold the head in place. Repositionable arm platforms are provided for steadying the physician's arms.

Park, U.S. Pat. No. 4,771,493, relates to an adjustable therapeutic pillow apparatus for applying a gentle traction force to the head, neck, and shoulder region of a user. The apparatus includes a base, first and second pillow members having spaced-apart convex pillow surfaces for engagement with the user, and means for fastening the pillow members to the base. The apparatus is adjustable in that both the lateral spacing of the pillow members and the overall length of the pillow members may be adjusted.

Laurin et al., U.S. Pat. No. 5,154,186, provides an apparatus for restraining a patient having a suspected spinal injury in the form of a spinal restraint including a rigid board, a plurality of restraining straps, a head support, a foot support, and carrying handles. The restraining straps extend laterally across the board from side portions thereof, the straps being longitudinally removable and laterally retractable. The head support is adapted for immobilizing the head of a patient and comprises a center support for supporting the back of the head of a patient and two side supports, one on each side of the central support, each one for supporting the side of the head of a patient and being movable between a support configuration and a loading and storing configuration in which the side support lies substantially flush with the center support.

Durham, U.S. Pat. No. 5,657,766, relates to a head immobilizing apparatus including a main board having a central portion and spaced apart side edge portions. Positioned along the side edge portions are apertures to accommodate backboard engaging straps and head immobilizing straps. The backboard engaging straps are provided to secure the main board to a backboard in an emergency medical situation. The head immobilizing straps can be operably positioned in a variety of locations depending upon the apertures for positioning the head immobilizing straps. A pair of removable head supports is operably attached to the central portion of the main board through a hook and loop material. A head cushion is positioned at the central most portion of the main board. The main board of the head immobilizer is constructed of a high strength corrugated disposable material and the upright cushions and head pillow are constructed of an open cell foam to absorb blood and bodily fluids during trauma of the head of the patient.

Henley, Jr., U.S. Pat. No. 4,794,656, relates to a backboard for immobilizing and transporting injured persons and a head restraining device for employment with such a backboard. The backboard includes a rigid support member, two head engaging members which are slidably received in a track attached to the rigid support member and latching assemblies to hold the head support members in a fixed position relative to the rigid support board. The head support members are designed to be positioned adjacent the head of an injured person who has been placed on the backboard, one head support member on each side of the head. The head support members may be completely removed from the track when not in use. The latching assemblies include a spring-biased member which engages the track, due to the spring bias, and holds the head-engaging member in a fixed position. The backboard may include body-strapping members which include a cloth strap, a ring slidably and rotatably retained by one end of the strap and a snap hook swivelly connected to each ring. The snap hooks are connectable to rods embedded in the handholds of the support board or to the rings of other strapping members. The backboards may include a foot support assembly which includes a footplate and two extension members. The footplate is rotatably attached to two extension members which in turn are slidably attached to the support board.

Klippel, U.S. Pat. No. 3,566,422, relates to a spine board apparatus with a short upper board member that is secured behind a patient's back and neck.

Gregory et al. U.S. Pat. No. 4,221,213, relates to a headpiece which is provided for the head end of a table on which a patient lies on a side to have bottom side of the head engage the headpiece. A plurality of pads are adjustable by the headpiece support so that the head is retained in a fixed position while a chiropractor makes a vertible adjustment.

Patil et al., U.S. Pat. No. 4,463,758, provides a frame having a platform or support including an area thereon for supporting a patient's head and for maintaining the patient's head in position.

Brock, U.S. Pat. No. 3,449,776, provides a collapsible telescoping head support mounted on a stretcher and has adjustable torso members mounted thereon. Straps extend through the head support and torso members for immobilizing a broken neck.

Darby, Jr., U.S. Pat. No. 3,650,523, relates to a restraining assembly for children including a rigid support board having a head portion at one end adapted to underlie the head of the patient and laterally adjustable head holding pads provided on the head portion.

Rankin, U.S. Pat. No. 3,672,364, relates to an anatomical, compressible weight immobilizer, having orthopedic strap tension weights which are adapted to immobilize a portion of an injured patient's anatomy against disposition or dislocation, while the patient is reclining. To the portable orthopedic strap tension weighted components is secured a cervical chin strap supplement, in one embodiment. The unit with attachments is applicable to a stretcher or hospital bed or operating table and may be used alternately in the transport of the patient or in the retention of the patient in position for examination, operation or ambulatory movement.

Each of these patents provides spinal and cervical immobilization apparatuses with various features. None of these patents, however, discloses or suggests an immobilization apparatus that provides for ease of adjustability without removal of parts, integrated parts, accommodation for a wide range of sizes, consideration for x-rays, symmetrical parts for easy manufacturing, safety locks, etc. It has therefore been found desirable to design a head immobilizer with the advantages as noted below.

In addition, debate continues in the medical community with respect to these head immobilizers in terms of the choice between device disposal and the corresponding trade-offs among ecological responsibility, infection risk and cost-efficiency. As a result of this debate, it has been found desirable to develop a head immobilization system that is essentially reusable but still low enough in cost to be disposed when significantly contaminated.

OBJECTS OF THE INVENTION

It is therefore an object of this invention to provide a head immobilizer system which overcomes the aforementioned deficiencies of the prior art.

It is therefore an object of this invention to provide a head immobilizer with a high level of motion restriction to the head and neck of a patient.

It is also an object of this invention to provide a head immobilizer with intuitive design with minimal product training needed.

It is another object of this invention to provide a head immobilizer with good visual and tactile access to eyes, ears, mouth, nose, and neck.

It is a further object of this invention to provide a head immobilizer with high level of x-ray transparency.

It is still another object of this invention to provide a head immobilization system which reduces the impact of equipment loss at a hospital when gear is left behind with patients awaiting X-ray clearance.

It is yet an object of this invention to provide a replacement pad and strap kit for a head immobilization system which allows the durable components to be reused indefinitely thereby reducing cleaning costs and minimizing exposure to pathogens.

It is yet a further object of this invention to provide a head immobilizer system which reduces material waste compared to disposable head immobilizers.

It is yet another object of this invention to provide a head immobilizer with durable components that can be cleaned and reused multiple times.

It is yet also an object of this invention to provide a head immobilizer that is fully adjustable to fit a large range of patients.

It is yet a further object of this invention to provide a head immobilizer that allows for quick application and readjustment.

It is still another object of this invention to provide a head immobilizer that promotes proper immobilization technique.

It is another object of this invention to provide a head immobilizer that has a small and compact design for easy storage.

It is yet another object of this invention to provide a head immobilizer with low cost compared to other head immobilization systems.

It is still another object of this invention to provide a head immobilizer that is easily attachable to and detachable from a spine board and is adaptable to fit a broad variety of board types.

It is another object of this invention to provide a head immobilizer system which is essentially reusable but still low enough in cost to be disposed of when significantly contaminated.

Various other objects, advantages and features of the present invention will become readily apparent from the ensuing detailed description and the novel features will be particularly pointed out in the appended claims.

SUMMARY OF THE INVENTION

An embodiment of the present invention includes a base headboard (or "headboard" or "base board") for providing a surface/interface for mounting one or more side blocks, which are adaptable for supporting one or more sides of a body part (e.g., the head). A soft material, such as a foam pad, is attached to the center portion of the headboard for providing comfortable support to the injured person's head. An elongated slot with teeth racks is disposed in the headboard on both sides of the injured person's head. The headboard also comprises straps for attaching to a spine board.

Two side head blocks are each removably attached to the headboard using a plunger-type lock that engages an elongated slot on a respective side of the headboard. These locks are engaged to the slots of the headboard through separate elongated slots in the head blocks, which may be aligned perpendicularly to the slots of the headboard. Advantageously, the head blocks may be adjusted by moving the engagement of the locks along a set of slots in the headboard and a set of slots in the head blocks, respectively. In addition, the head blocks may be rotated around the locks. Consequently, the present invention allows the blocks to be located at any point on the base within a predetermined limit of motion. The head blocks are, thus, adjustable so as to accommodate the various size features of a particular patient while promoting proper immobilization technique by minimizing movement of, and possible trauma to, the cervical spine of the patient.

Each head block has a universal configuration such that there is no difference between a left and a right head block. When attached to the headboard, each head block includes an upright planar portion with a soft material (foam pad) attached thereto for fitting a side of the injured person's head and a horizontal portion that includes the aforementioned slot for engaging the headboard. The upright planar portion includes an arch opening that exposes the side of the injured person's head so as to allow access thereto for injury diagnosis by emergency medical personnel. The arch opening also improves the x-ray transparency of the injured person's head, thus allowing emergency medical personnel to take x-ray of an injured person's head while it is immobilized. The upright planar portion further includes a curvilinear (bell-shaped) cross section for improving x-ray transparency. For easy storage, these portions of the head block may be removed from the base and disengaged to a flat position when not in use.

The head immobilizing apparatus may be adjusted with ease to fit a patient of any size/age (of at least two years old) without removing any of its parts. This integration of parts prevents parts from being lost or misplaced, and allows for quick immobilization of a patient without the need to locate individual parts. The locks for locking the head blocks include at least two locking stages, whereby individual directions of adjustment for the head blocks may be locked in place thus allowing for a better fit on a patient.

Attachment straps are incorporated to the headboard for attaching to a spine board. Head immobilizing straps may be extended across the forehead and chin of the injured person between the head blocks. According to an embodiment of the invention, the head immobilizing straps are angled such that the pressures thereof are oriented toward the mandible joint, which reduces discomfort while enabling emergency medical personnel to open the mouth of the injured person.

The cooperating attachment straps and/or head straps may further comprise cooperating hook or loop material or an adhesive double sided tape, such material may also be attached to a bottom surface of the head pad means for attaching the head pad means to the headboard, and a surface of the head block pads for attaching the head block pads to the respective head blocks.

The preferred soft material for the headboard and head blocks (foam pads) is, thus, readily removable from the headboard and head blocks for easy replacement. In accordance with an embodiment of the invention, a disposable kit may include two head block pads, a headboard pad and two head straps. A cervical collar may also include neck and chin pads and an attachment strap that are removably attached from a disposable kit. Thus, the pads and straps may be easily removed, decontaminated and/or replaced when contaminated without having to replace any of head blocks, headboard or cervical collar.

The headboard is preferably constructed of a molded plastic material and configured such that an elongated slot extends axially across the headboard perpendicular to the side edges on either side of a center portion thereof, and may further include a spineboard strap enabling the headboard to be attached to the spineboard.

The head pad means may further comprise a pair of universally configured pads, each pad having spaced apart upright side surfaces extending perpendicularly from a bottom and merging at a pair of ends. The head pad means and the head support means are preferably constructed with foam of a color dissimilar to the color of human blood.

The immobilizing strap means may further comprise a buckle enabling a free end of the immobilizing strap means to be inserted therethrough and folded over to attach to its length.

In accordance with another embodiment, the features of the headboard may be directly incorporated to a spineboard, thereby allowing head blocks to be attached thereto without the need of a separate headboard.

The invention accordingly comprises the apparatus embodying features of construction, combination(s) of elements and arrangement of parts, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings(s), wherein like reference numerals denote like elements and parts, in which:

FIGS. 2A and 2B illustrate attaching a head block of the head immobilization apparatus to a base part and three ways for adjusting the head block before locking in accordance with an embodiment of the present invention;

FIG. 3 illustrates a locking device for attaching a head block of the head immobilization apparatus in accordance with an embodiment of the present invention;

FIG. 4A illustrates the underside of a locking device for attaching a head block of the head immobilization apparatus in accordance with an embodiment of the present invention;

FIGS. 7 to 11 illustrate the steps for applying the head immobilization apparatus to an injured person loaded on a spine board in accordance with an embodiment of the present invention;

FIG. 12 is a view of the head immobilization apparatus as attached to a spine board in accordance with an embodiment of the present invention;

FIGS. 13A, 13B, and 13C illustrate storage and deployment positions of a head block of the head immobilization apparatus in accordance with an embodiment of the present invention;

FIGS. 18A and 18B is a cross-sectional view of the attachment of a head block to a spine board using an attachment device in accordance with an embodiment of the present invention;

FIGS. 19A, 19B, and 19C illustrate the x-ray transparent structure of a head block in accordance with an embodiment of the present invention;

FIGS. 20A, 20B, 20C, and 20D illustrate replaceable elements of a head immobilization apparatus in accordance with an embodiment of the invention;

FIG. 21 is a view of an embodiment of a multi-size or position cervical collar constructed according to the principles of the invention, as viewed from the interior side of the collar.

DETAILED DESCRIPTION OF THE PREFERRED EMBODIMENTS

Figure 1:
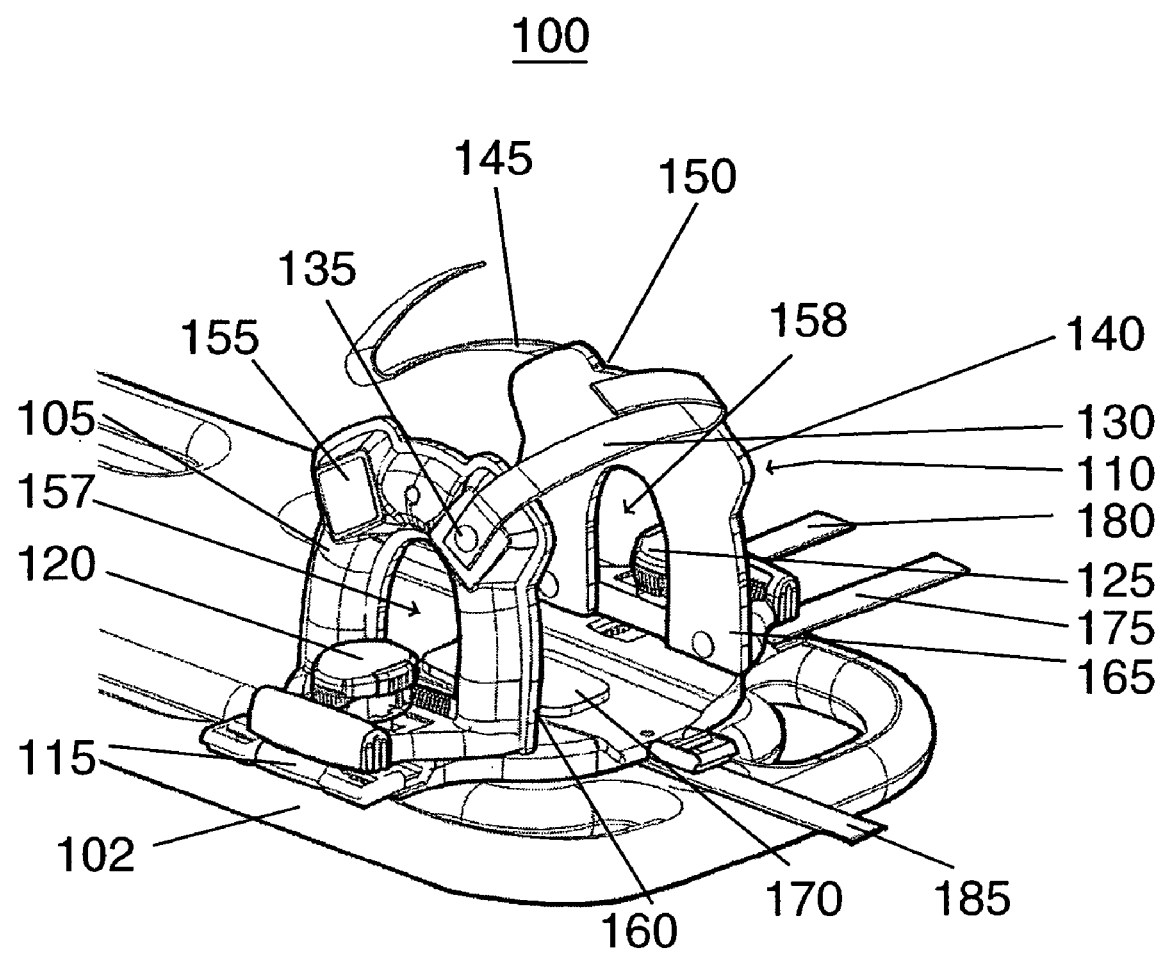
FIG. 1 depicts a head immobilization apparatus assembled for attaching to a spine board in accordance with an embodiment of the present invention.

FIG. 1 depicts an assembled head immobilization apparatus 100 for attaching a spine board 102 in accordance with an embodiment of the invention. As illustrated in FIG. 1, head immobilization apparatus 100 comprises two head blocks 105 and 110 placed on either side of an injured person's head (see FIG. 11). It is noted that, in accordance with an embodiment of the invention, blocks 105 and 110 are of a uniform design so that they may be interchanged with each other on either side of the injured person's head. It is, thus, noted that the following description and corresponding Figures regarding either block 105 and 110 may be applied to other, and that duplicate description may be omitted.

Blocks 105 and 110 are fixed to a headboard (or base) 115 for supporting the back of the injured person's head by pressing down on plunger-type locks 120 and 125. Blocks 105 and 110 can be released for readjustment or removal by depressing a respective lever on lock members 120 and 125, which will be described in further detail below. Additional head motion restraint is achieved by connecting a strap 130, which is attached to block 110 by a rivet 135, to block 105 by a releasable fastener 140 across the forehead of the injured person (see FIG. 11), and connecting a corresponding strap 145, which is attached to block 105 by a rivet 150, across the chin back to block 110 by a releasable fastener 155 (see FIG. 11). In accordance with the invention, rivets 135 and 150 and fasteners 140 and 155 may be rotatable or disposed at a predetermined angle so that straps 130 and 145 connected across the forehead and chin of the injured person may be angled to accommodate a wider range of head sizes. In addition, the angles of straps 130 and 145 orient the pressures thereof toward the mandible joint, which reduces discomfort while enabling emergency medical personnel to open the mouth of the injured person. Blocks 105 and 110 also include arch openings 157 and 158, respectively, for providing access to the sides of the injured person's head, including the ears. The arch opening also improves the x-ray transparency of the injured person's head, thus allowing emergency medical personnel to take x-rays of an injured person's head while it is immobilized. In the illustrative embodiment, fasteners 140 and 155 are hook and loop fabric tape-style fasteners that are attached to blocks 110 and 105, respectively, for fastening straps 130 and 145. It is noted that any fasteners, such as buttons, additional straps, etc., may be used.

To ensure comfort, foam pads 160 and 165 are riveted to blocks 105 and 110 on their surfaces that come in contact with the patient. An additional foam pad 170 is attached to headboard 115 via double-sided tape to cushion the back of the head and to prevent sliding. Pads 160, 165, and 170 may be made with foam of a color dissimilar to the color of human blood. Advantageously, a used pad (160, 165, or 170) may be easily identified and removed to be decontaminated and/or replaced.

Figure 6A:
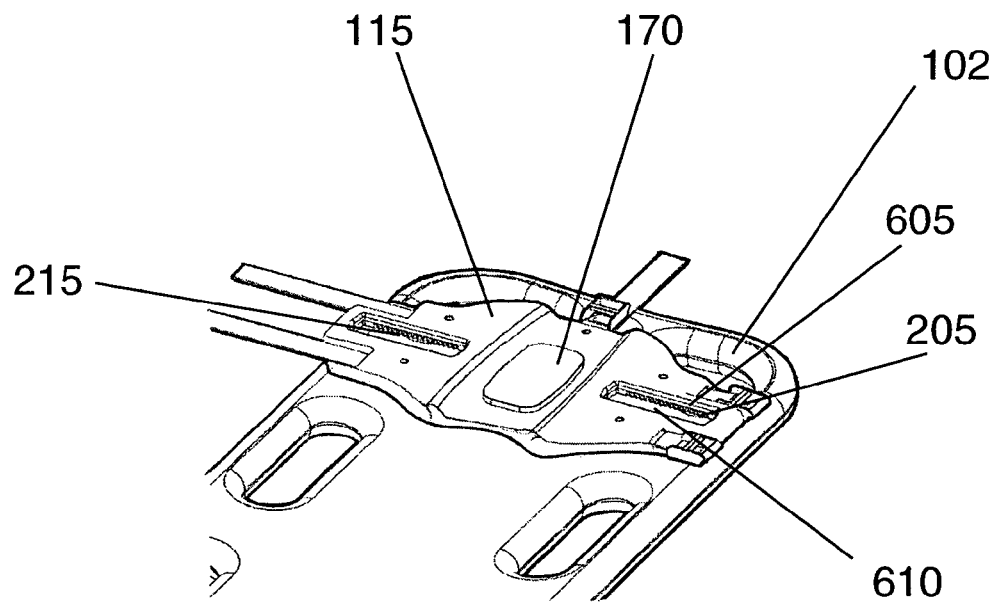
FIG. 6A depicts a base part of the head immobilization apparatus attached to a spine board in accordance with an embodiment of the present invention.
Figure 6B:
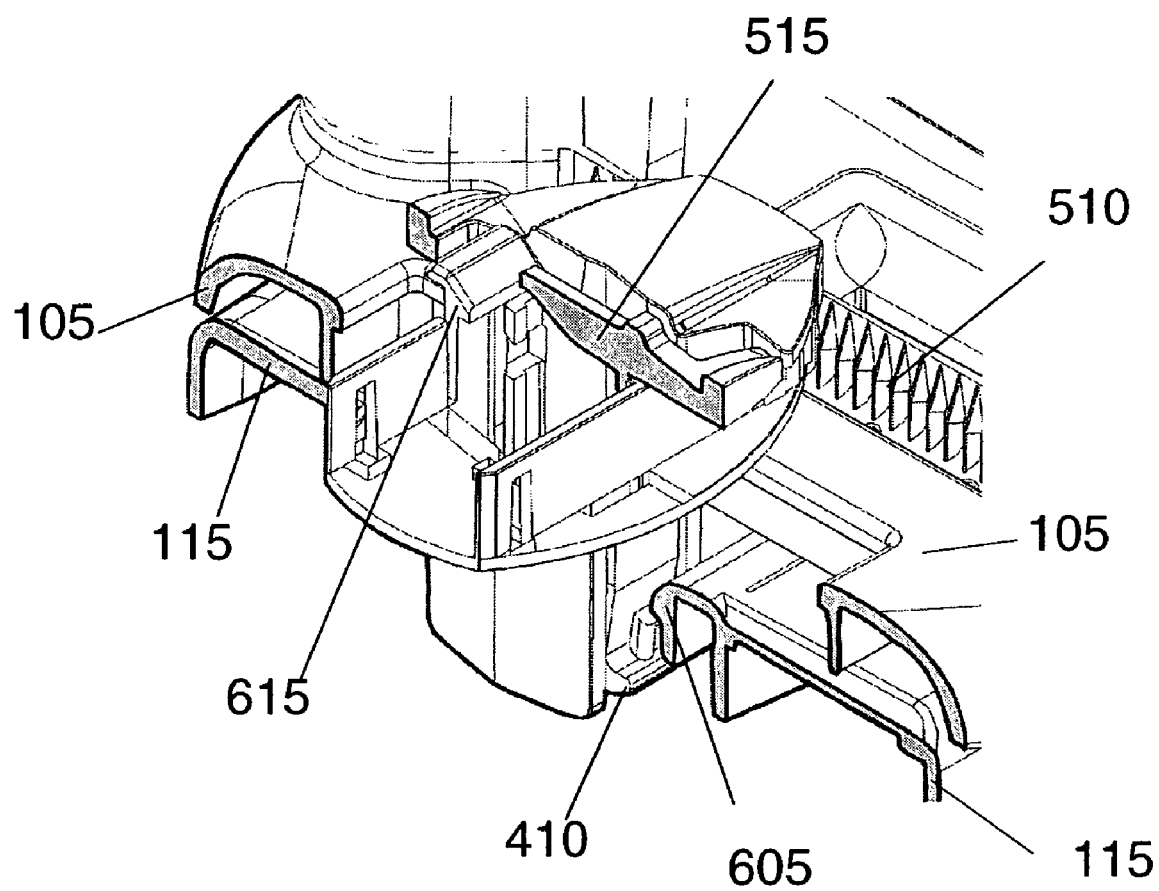
FIG. 6B shows a view of an interaction between a locking device and a head block of the head immobilization apparatus in accordance with an embodiment of the present invention.
Figure 7:
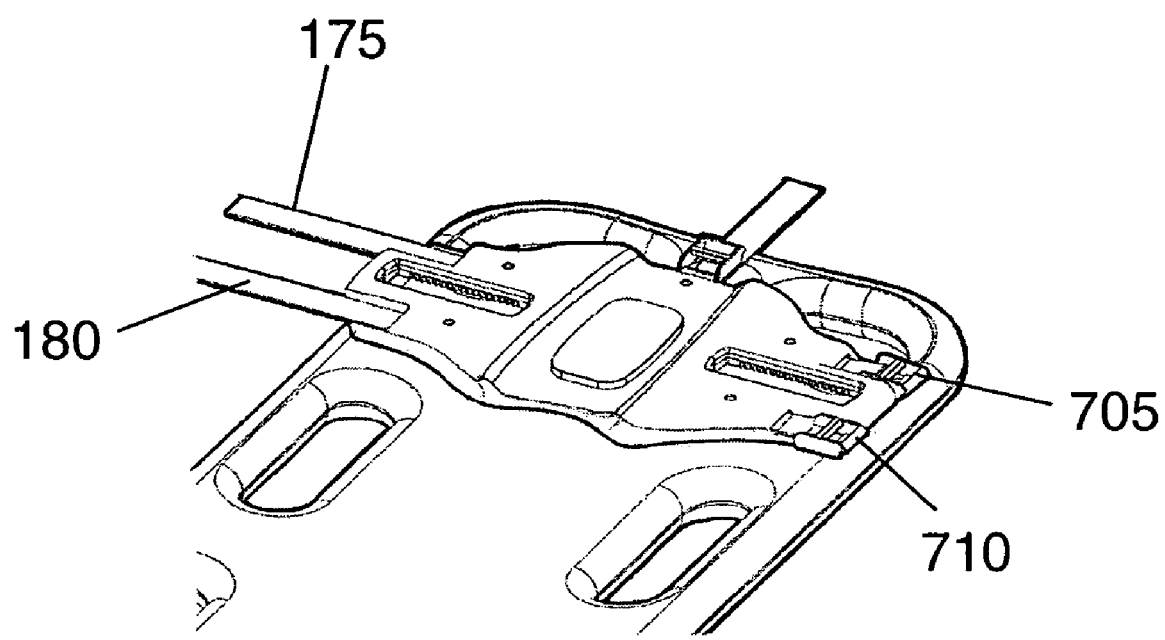

As shown in FIG. 1, headboard 115 may be attached to a spine board 102 by means of 3 straps 175, 180, and 185 (see also FIGS. 6, 7, and 12).

Figure 2A:
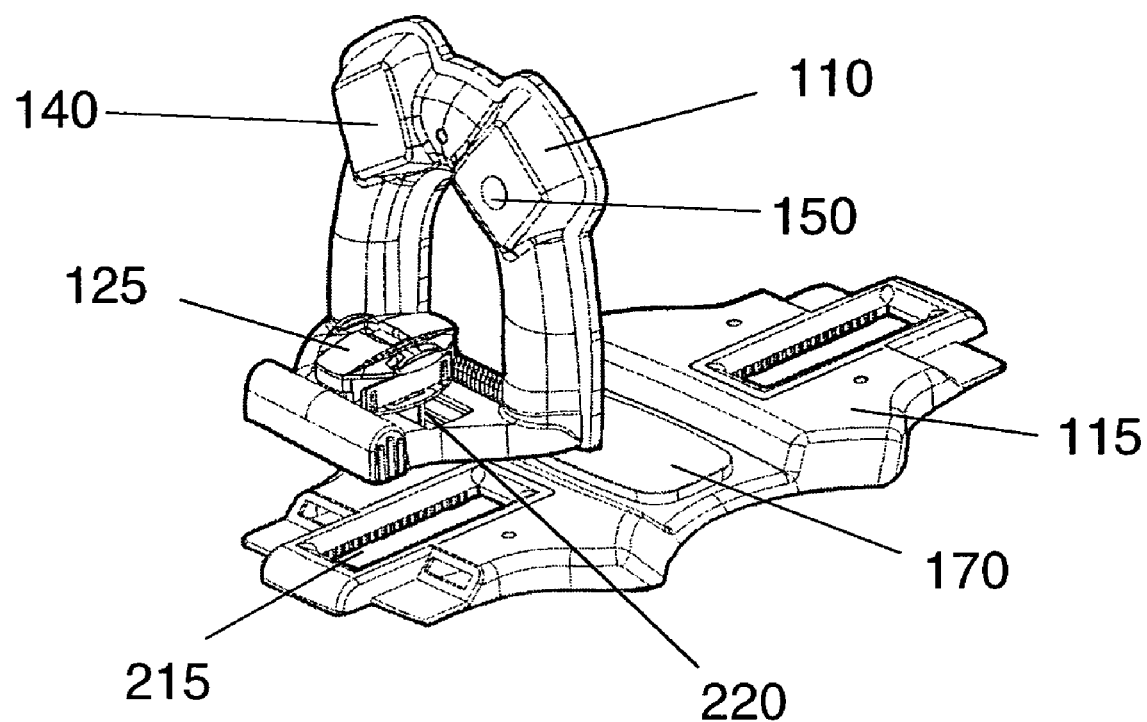

FIGS. 2A and 2B depict blocks 110 and 105, respectively, being attached to headboard 115 using lock members 125 and 120, and illustrate the three ways that blocks 110 and 105 may be adjusted to fit the head of an injured person. Illustratively, as shown in FIG. 2B, block 105 is attached to headboard 115 by engaging lock member 120 to slot 205 in headboard 115 through a slot 210 in block 105. Block 105 may be slid laterally (to and from the center of headboard 115) along slot 205, longitudinally along slot 210, and rotated relative to headboard 115 in 5 degree increments (−/+10 degree range) around lock member 120. Correspondingly, as shown in FIG. 2A, block 110 may be operated in a similar manner on the opposite side of foam pad 170 along slot 215 of headboard 115 and slot 220 of block 110. Thus, blocks 105 and 110 are respectively slid within a respective single slot 205 and 215 provided on both sides of foam pad 170 of headboard 115.

Figure 4B:
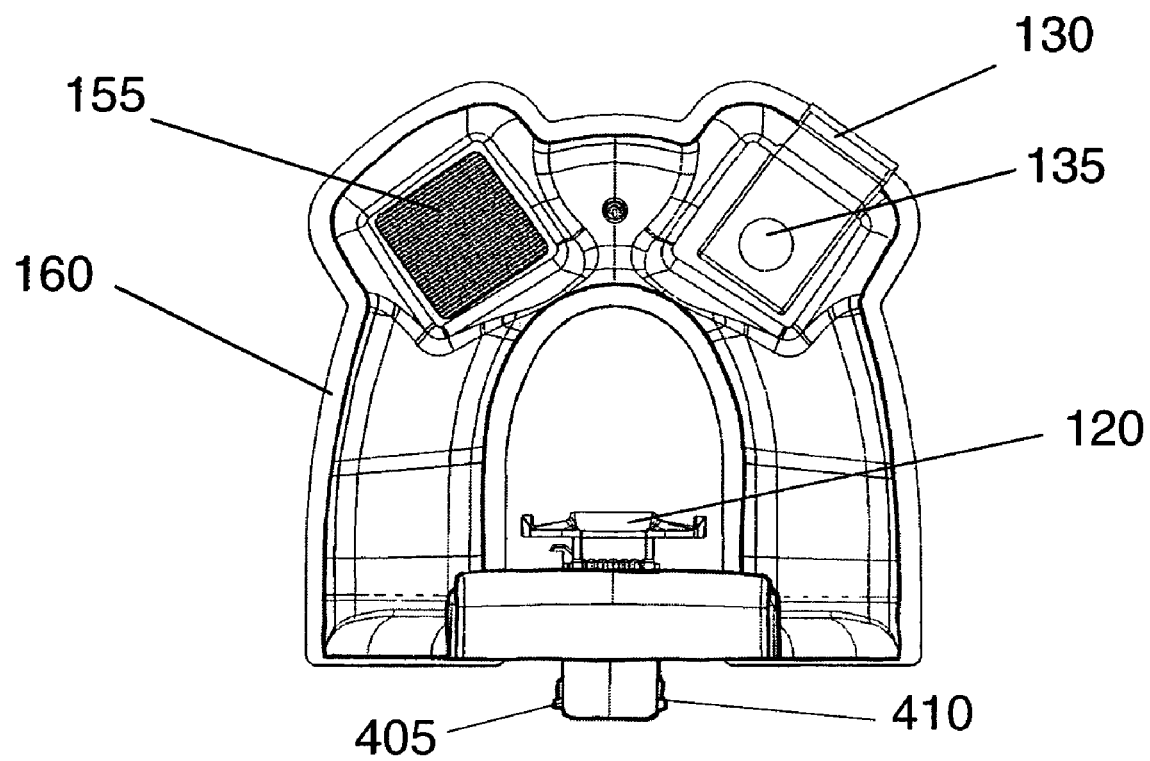
FIG. 4B shows a view of the locking device and head block in accordance with an embodiment of the invention.

FIGS. 3, 4A, and 4B illustrate the two-part construction of lock member 120, which enables a fit adjustment stage and a locking stage. By pushing lock member 120 down to a fit adjustment stage while in the configuration illustrated in FIG. 2, block 105 is physically connected to headboard 115 but can still be longitudinally and laterally adjusted along slot 210 and rotationally adjusted around lock member 120. The locking stage, enabled by further pushing down on lock member 120, fixes block 105 in place.

Figure 5:
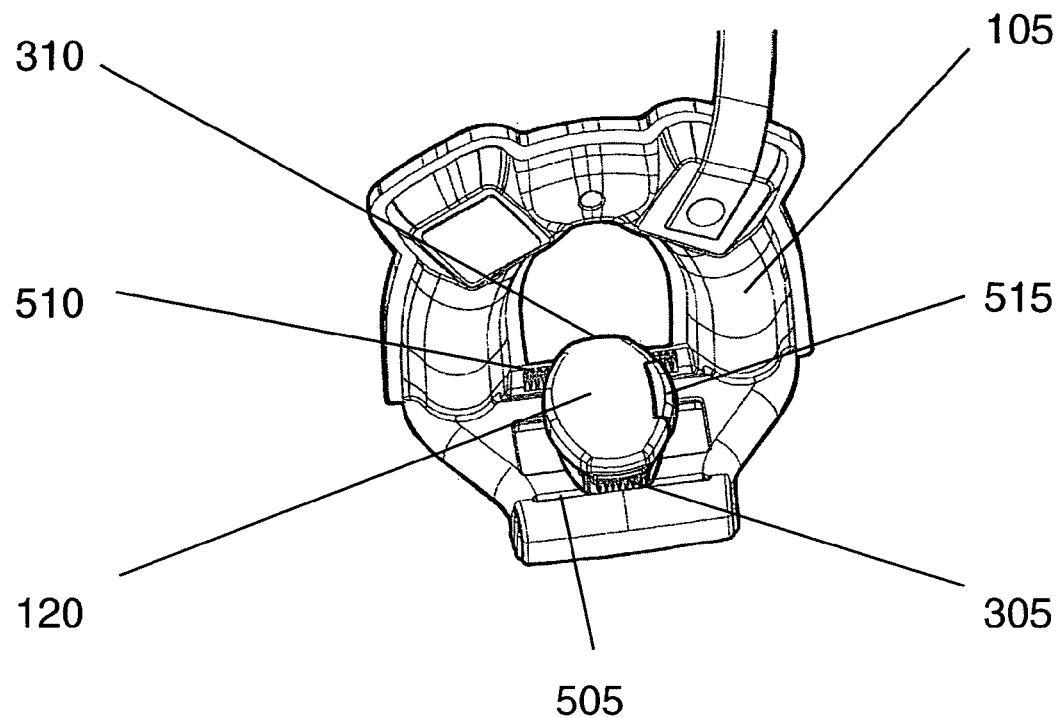
FIG. 5 illustrates an interaction between a locking device and a head block of the head immobilization apparatus in accordance with an embodiment of the present invention.

FIGS. 5, 6A, and 6B illustrate parts of block 105 and headboard 115, respectively, that interact with lock member 120 for locking block 105 to headboard 115.

With reference to FIGS. 4A, 4B, 6A, and 6B, the fit adjustment stage is engaged with two flexible fingers 405 and 410 on the lower half of lock member 120 each engaging slot 205 of headboard 115, thus locking block 105 vertically in place. In the fit adjustment stage, block 105 may still be rotated around lock member 120 and slid longitudinally along slot 210 of block 105 and laterally along slot 205 of headboard 115.

Referring now to FIGS. 3, 5, and 6B, the locking stage is engaged with rows of teeth 305 and 310 on the upper part of lock member 120 each locking into a respective rack of teeth 505 and 510 on block 105, thus fixing block 105 longitudinally and rotationally. Lateral motion is also fixed by further deflecting flexible fingers 405 and 410 into respective racks of teeth 605 and 610 in slot 205 of headboard 115.

In the locking stage, block 105 can be unlocked for removal or for readjustment (in the adjustment stage) by pressing an unlock lever 515, as shown in FIG. 5, on the upper lock part of lock member 120 and lifting up. Pressing lever 515 disengages it from a locking tab 615 (shown in FIG. 6B) in lock member 120 and disengages each set of teeth 305, 310, 405, and 410 from their respective rack 505, 510, 605, 610 by simply lifting lock member 120, thus allowing block 105 to once again ratchet along the surface of headboard 115 with three degrees of freedom, as illustrated by FIGS. 2A and 2B. In the unlocked state, block 105 can also be disconnected from headboard 115 by pulling up on it. Correspondingly, the operation of block 110 is the same as that of block 105 described above.

FIGS. 7 to 11 illustrate, step-by-step, the immobilization of a patient using head immobilization apparatus 100 according to the above-described embodiment of the invention. As shown in FIG. 7, the first step is to attach base headboard 115 to one end of spine board 102. Straps 175 and 180, which are riveted to headboard 115 on one side, loop around and under spine board 102 and fasten back to headboard 115 via clips 705 and 710 on the other side.

With headboard 115 in place, spine board 102 can be easily stored with no need to remove headboard 115 until cleaning is required. As shown in FIG. 8, the patient is placed onto spine board 102 with his head centered on foam pad 170. Each block (105 and 110) and lock member (120 and 125) assembly is then placed into headboard 115 on either side of the head. Block adjustments are then made in an effort to restrict head motion and to center the ear in arch opening 157, as shown in FIG. 9. Once the desired position of a block (105) is established, the user pushes down on the lock member (120), fixing the block (105) in place, as illustrated in FIG. 10. Preferably, an audible sound and/or visual cues may be provided to notify the user when the lock member (120) is fully engaged.

As shown in FIG. 11, with both blocks (105 and 110) fixed snuggly against the patient's head, the two head-straps (130 and 145), made of loop material, are pulled taut across the chin and the forehead and fastened to the adjacent block (105 and 110) where a patch of fastening material (140 and 155) is provided. In this condition, the patient's head is fully immobilized.

FIG. 12 is an exploded view of head immobilization apparatus 100 in accordance with an embodiment of the invention. For clarity of illustration, block 110 and lock member 125 have been omitted from FIG. 12 with the understanding that they correspond to block 105 and lock member 120, respectively. As shown in FIG. 12, block 105 is attached to headboard 115 by engaging lock member 120 to slot 205 in headboard 115 through slot 210 in block 105.

Figure 13C:
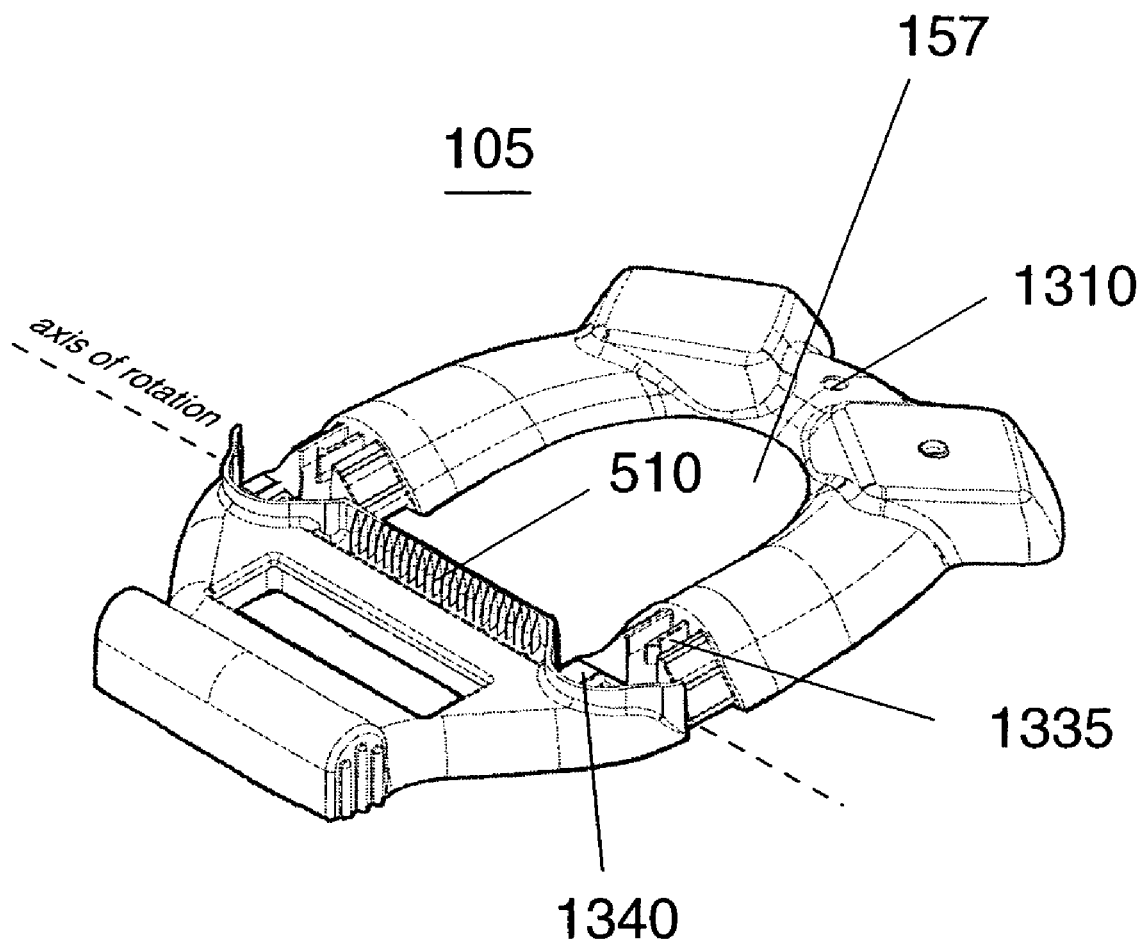

FIGS. 13A, 13B, and 13C illustrate a flat storage position of head block 105 (and 110) (FIG. 13A) and an upright deployment position thereof (FIG. 13B) in accordance with an embodiment of the invention. As shown in FIG. 13A, head block 105 comprises a hinge portion 1305 that allows an upper portion 1310 of block 105 to rotate 90 degrees to the upright deployment position shown in FIG. 13B. Corresponding snap hooks 1315 and 1320 and snap holes 1325 and 1330 snap into engagement and lock head block 105 in the upright deployment position of FIG. 13B. It is noted that the snap engagement of hooks 1315 and 1320 to holes 1325 and 1330 can be disengaged to restore block 105 to the flat position of FIG. 13A for storage. Referring back to FIG. 1, it is further noted that strap 145, rivet 150, and releasable fastener 140 are arranged on block 105 in an identical manner as strap 130, rivet 135, and releasable fastener 155 of block 110. Alternatively, as illustrated by FIGS. 12, 13A, and 13B, head block 105 may comprise strap bridges 1205 and 1210 for accommodating the equivalent of straps 130 and 145 described above. As described before, blocks 105 and 110 may be interchanged on either side of the injured person's head. In other words, head blocks 105 and 110, according to an embodiment of the present invention, are identical with no differentiation between left and right head blocks. Furthermore, blocks 105 and 110 may be molded flat, as shown in FIG. 13A, and snapped into place upon deployment, as illustrated by FIG. 13B. Consequently, the manufacture of head blocks 105 and 110 is simplified. FIG. 13C illustrates an alternative embodiment for a detachable snap feature 1335 (which operates in a similar manner as snap hooks 1315 and 1320 and snap holes 1325 and 1330 shown in FIG. 13A) and hinge mechanism 1340 (which corresponds to hinge portion 1305 shown in FIG. 13A) for the above-described rotating engagement of upper portion 1310 of head block 105 from the flat storage position (shown in FIGS. 13A and 13C) to the upright deployment position (shown in FIG. 13B).

In accordance with an embodiment of the invention, upper portion 1310 of head block 105 (and 110) is taper-walled, having a bell-shaped cross section, with an arch opening 157 (and 158, as shown in FIG. 1 and described above). The shape of upper portion 1310, in accordance with the invention, allows x-rays be taken on the cervical spine region of a patient with minimal artifacts, and unimpeded through arch opening 157 (and opening 158 of corresponding head block 110 shown in FIG. 1). Details of the bell-shaped cross section of upper portion 1310 and its reduction of x-ray artifacts will be further described below with reference to FIGS. 19A, 19B, and 19C.

As described above, according to one embodiment of the invention, blocks 105 and 110 are attached and locked to separate base headboard 115, which can be attached to spine board 102 using straps 175, 180, and 185 as shown in FIGS. 1 and 6. Advantageously, straps 175, 180, and 185 are disposed in such a manner that headboard 115 may be attached to a spine board (102) of any design or manufacture.

Figure 14:
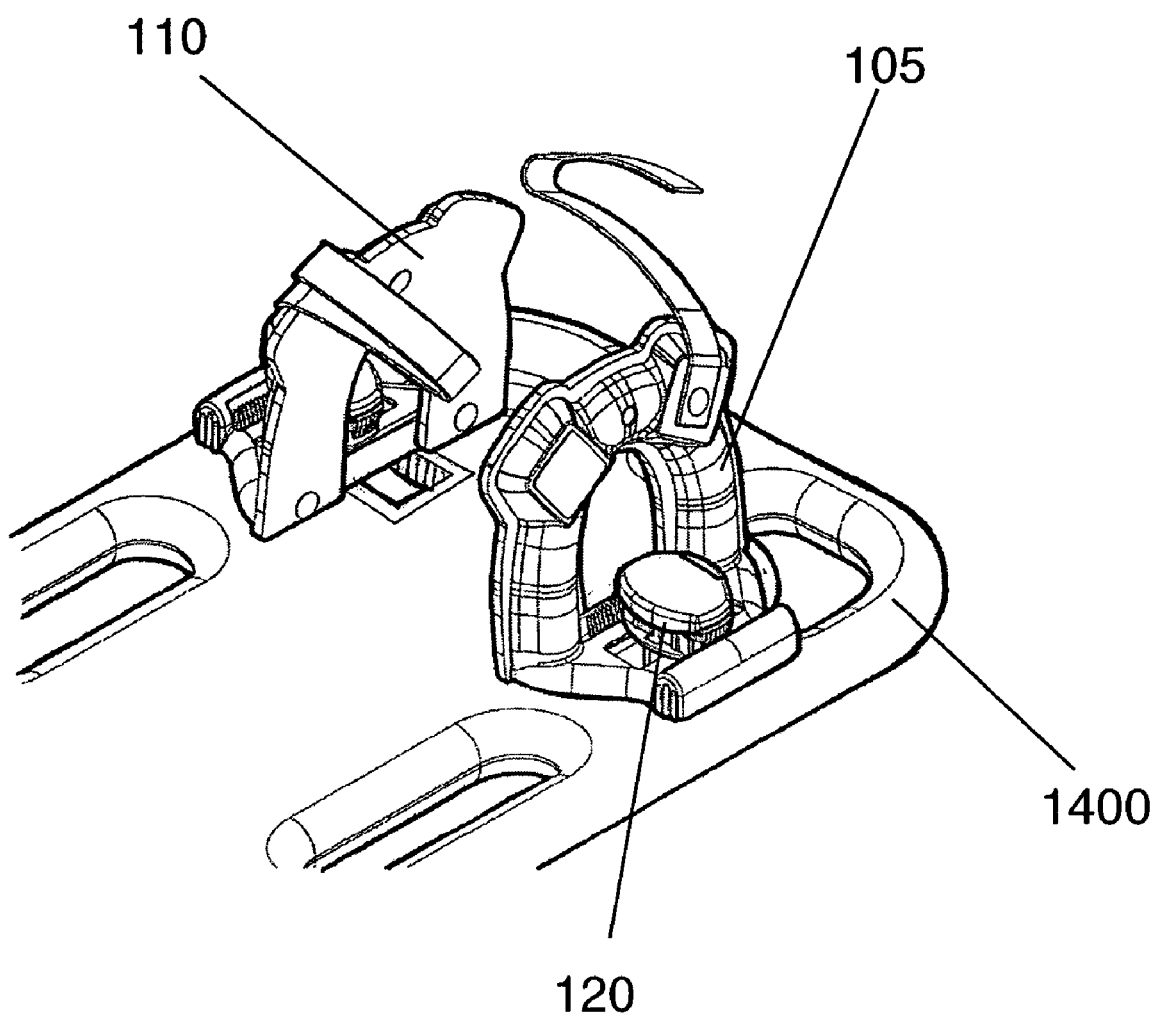
FIG. 14 depicts an assembled head immobilization apparatus on a spine board in accordance with an embodiment of the present invention.
Figure 15:
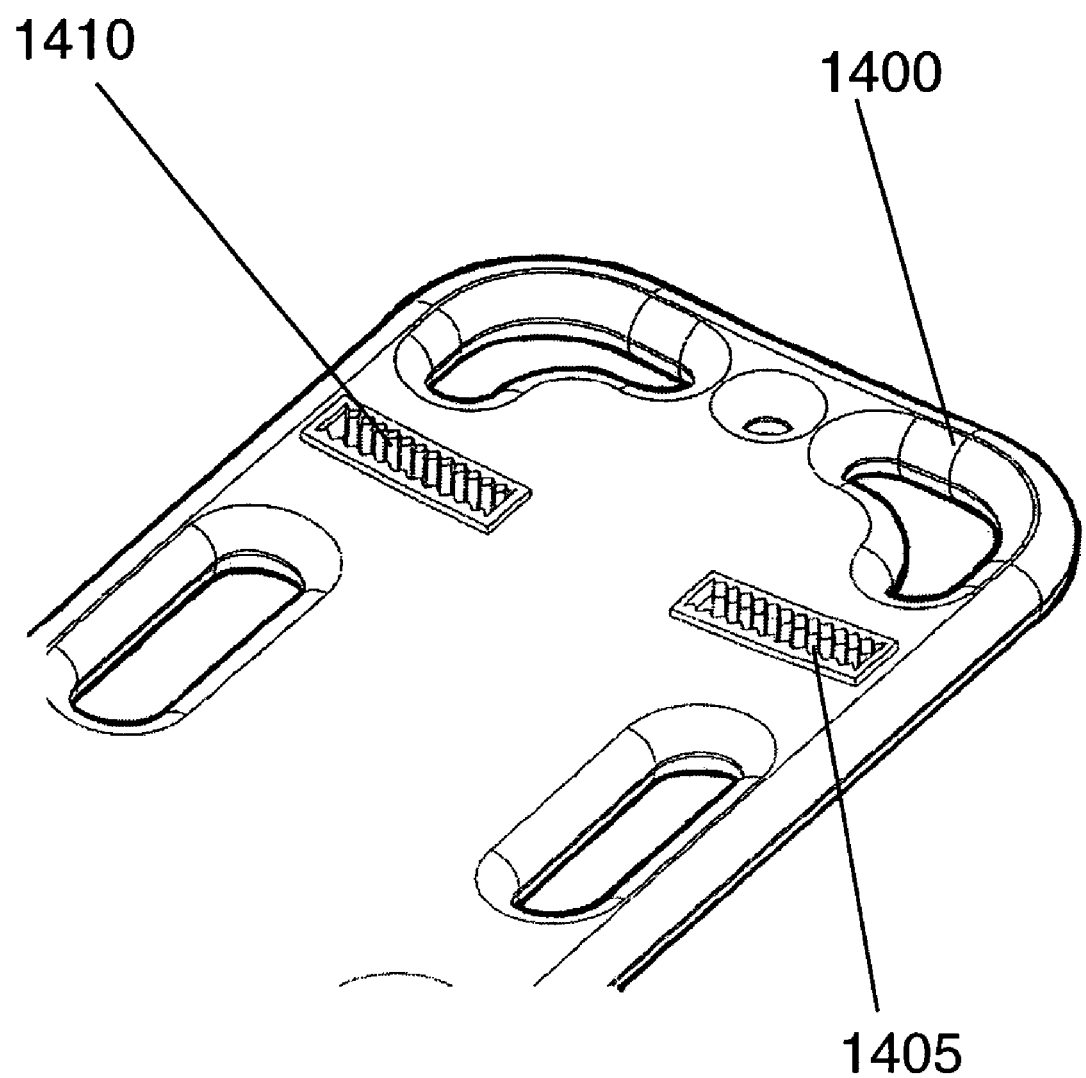
FIG. 15 depicts a head immobilizer mounting portion of a spine board of FIG. 14 in accordance with an embodiment of the present invention.

In accordance with another embodiment, the aforementioned features of headboard 115 may be incorporated directly to spine board 102, whereby head blocks 105 and 110 may be attached directly to spine board 102. FIG. 14 illustrates blocks 105 and 110 attached directly to a spine board 1400 using lock member 120 and lock member 125 (not shown), thus omitting base headboard 115. FIG. 15 depicts spine board 1400 without blocks 105 and 110 attached thereto. As shown in FIG. 15, spine board 1400 includes a single slot 1405 and 1410 to engage a respective head block, which are functional equivalents of slots 205 and 215 of headboard 115. Block 105 may be attached to spine board 1400 by engaging lock member 120 to a slot 1405 in spine board 1400 through a slot 210 in block 105. Block 105 may be slid laterally (to and from the center of spine board 1400) along slot 1405, longitudinally along slot 210, and rotated relative to spine board 1400 in 5 degree increments (−/+10 degree range) around lock member 120. Correspondingly, block 110 may be operated in a similar manner along slot 1410. Thus, blocks 105 and 110 may be respectively slid within a respective single slot 1405 and 1410 provided on both sides of a center portion of spine board 1400. By decreasing the total number of parts (base headboard 115) and attachments thereof (straps 175, 180, and 185), this embodiment reduces the storage space required, and improves x-ray clarity and patient immobilization.

The lock member (120 and 125) for engaging a head block (105 and 110) to a base board (115 or 1400) described thus far is based on the positive engagement of meshes of gear teeth. When a head block (105 and 110) is connected to the base board (115 or 1400) using the lock member (120 and 125)(where a bottom portion of the lock member may include a mechanism for movably attaching to a slot in the base board through a slot in the head block), the head block may be adjusted longitudinally (along the long axis of the backboard), laterally (towards the centerline of the board), and rotationally around a locking mechanism (120 and 125). By pushing down on the locking mechanism (120 and 125), the user may lock the three adjustment components into place. This locking step causes two locking fingers to deflect into the gaps between rows of teeth in the base, holding the head block (105 and 110) in position laterally. This user action is also simultaneously meshing two sets of teeth on the handle with teeth on the head block (105 and 110), effectively fixing the head block (103 and 110) longitudinally and rotationally. A lock member (120 and 125) based on mechanical engagement is very strong and can consistently perform its function in wet, hot, and cold environments.

In accordance with an alternative embodiment, a head block (105 and 110) may be locked in position by friction. Instead of relying on the interference of teeth to restrict motion, high friction planar surfaces that have enough pressure exerted normal to the surfaces thereof may be used to eliminate motion between them. This alternative locking mechanism may be used particularly for the locking of a head block (105 and 110) laterally on a base board (115 or 1400). When the user pushes down on a handle, as will be described in detail below, instead of deflecting teeth into the spaces between other teeth, one flat surface is pushed against another with enough force to eliminate the possibility of slip. The contact surface may be roughened to provide a high-friction interface or a compressible material such as synthetic rubber or other elastomer could be employed to ensure a solid grip. On a microscopic level, frictional locking is very similar to the large teeth rack system: miniature "teeth" are interlocking on the adjacent surfaces thereby restricting motion. It is the high force normal to the contact surfaces that is the major difference between the two techniques. For this alternative embodiment, the part complexity is greatly reduced because rows of teeth are no longer needed.

Figure 16:
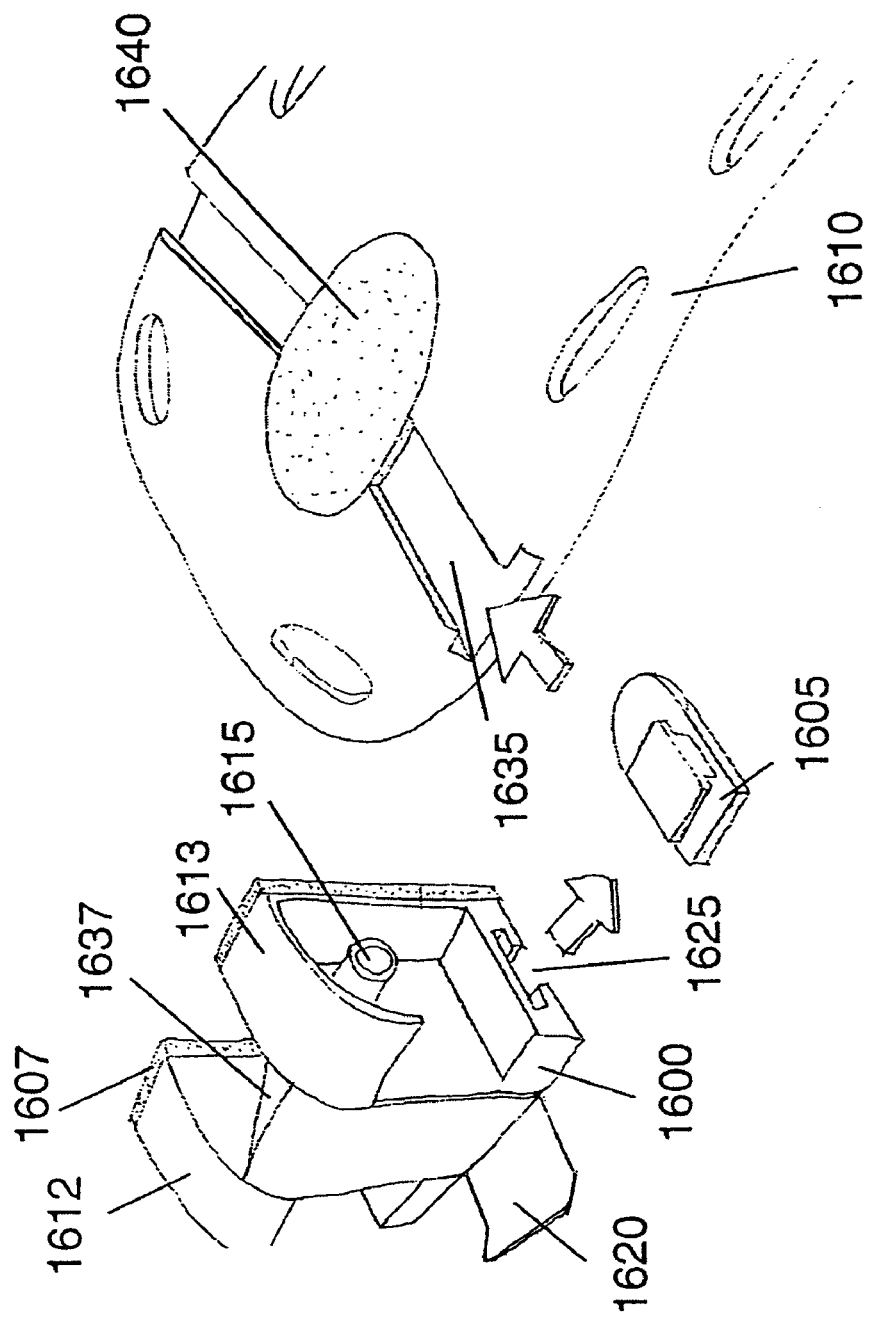
FIG. 16 illustrates the attachment of a head block to a spine board using an attachment device in accordance with an embodiment of the present invention.

FIG. 16 depicts a head block 1600, an interfacing block 1605, and a spine board 1610 in accordance with an illustrative embodiment of the above-described friction-based locking mechanism. As shown in FIG. 16, head block 1600 includes detachable foam pad 1607 (which is an equivalent of foam pad 160), a tape guiding surfaces 1612 and 1613 a tape receiving holder 1615, a cam lock 1620, and a notch 1625 for slidably accommodating interfacing block 1605. A tape dispenser (not shown) is disposed under tape guiding surface 1612. According to the invention, interfacing block 1605 may be permanently mounted on head block 1600. As further illustrated in FIG. 16, head block 1600 is attached to spine board 1610 by sliding interfacing block 1605 into a track 1635 of spine board 1610. Head block 1600 may be adjusted laterally (to and from center of spine board 1610), longitudinally (by sliding head block 1600 on interfacing block 1605 along notch 1625), and rotationally (by rotating around interfacing block 1605) before being locked into place on spine board 1610 by lowering cam lock 1620. Head block 1600 also comprises slanted surface 1637, which is the functional equivalent of arch opening 157, for providing emergency medical personnel access to the side of the injured person's head, including the ear. Spine board 1610 includes a removable head pad 1640, which is similar to head pad 170. It is noted that head block 1600 is attached directly to spine board 1610, corresponding to the embodiment shown in FIGS. 14 and 15.

Figure 17:
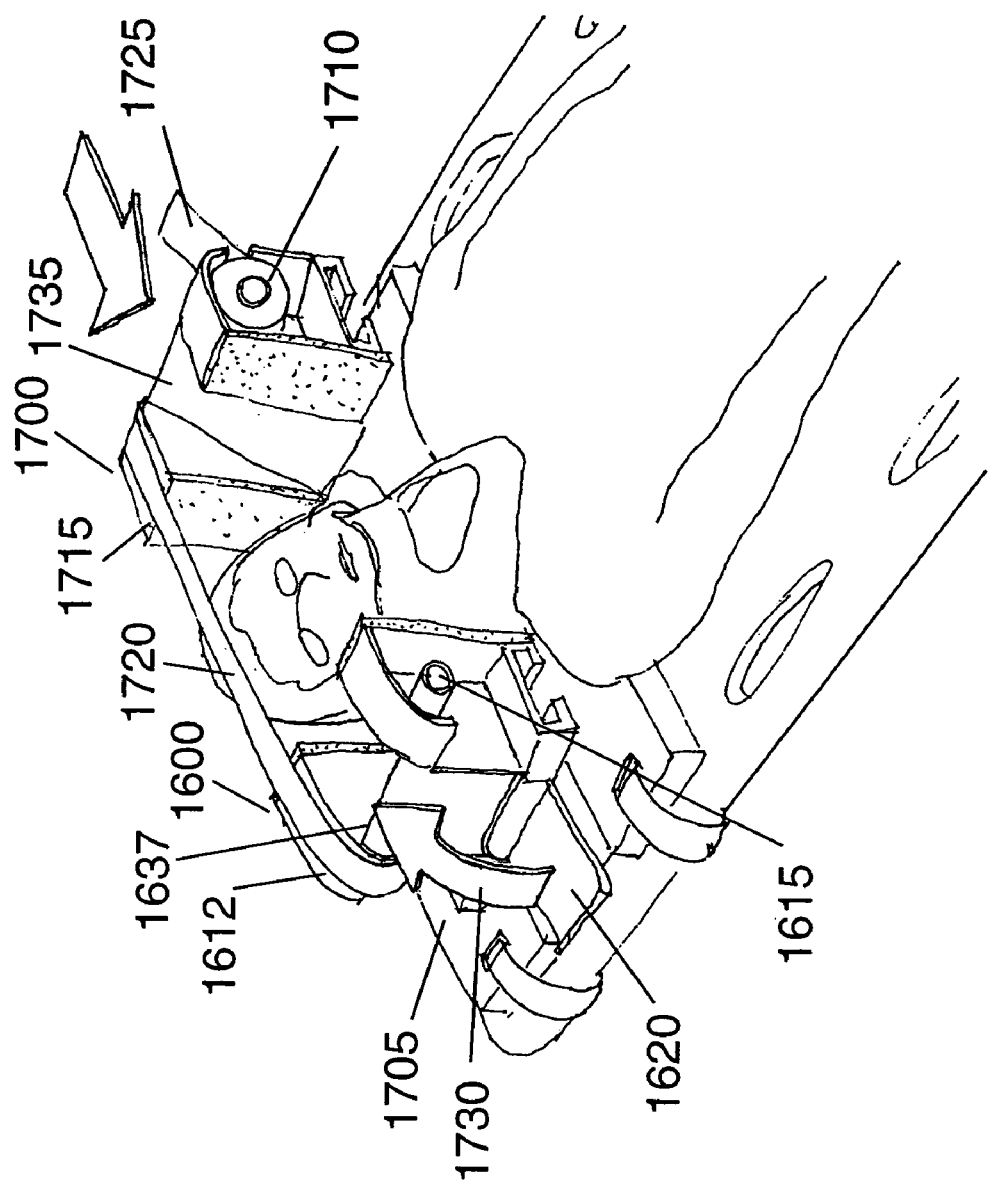
FIG. 17 illustrates applying a head immobilization apparatus to an injured person loaded on a spine board in accordance with an embodiment of the present invention.

FIG. 17 illustrates head block 1600 and a corresponding head block 1700 attached to spine board 1610 using a headboard 1705 (similar to headboard 115) so as to immobilize an injured person's head in accordance with an alternative embodiment of the invention. As shown in FIG. 17, head block 1700 comprises a tape dispenser 1710 that is similar to the dispenser under tape guiding surface 1612. A tape receiving holder similar to holder 1615 is disposed under tape guiding surface 1715 of head block 1700. As illustrated by FIG. 17, a tape 1720 from the dispenser under guiding surface 1612 is extended across the forehead of the patient and removably attached to the receiving holder under guiding surface 1715 of head block 1700. Similarly, tape 1725 from dispenser 1710 may be extended across the chin of the patient and removably attached to receiving holder 1615. Thus, tapes 1720 and 1725 perform the function of fitting head blocks 1600 and 1700 to the sides of the patient's head, which is similar to that of straps 130 and 145. Similar to rivets 135 and 150 and fasteners 140 and 155, the tape dispensers and receivers may be rotatable or disposed at a predetermined angle so that tapes 1720 and 1725 connected across the forehead and chin of the injured person may be angled to accommodate a wider range of head sizes. Tapes 1720 and 1725, integrated in blocks 1600 and 1700, allow for easy strapping of the patient's head. As described before, cam lock 1620 is used to lock block 1600 into position, and may be disengaged by lifting in the direction of arrow 1730. As further illustrated by FIG. 17, slanted surface 1637 and a corresponding slanted surface 1735 of head block 1700 provide emergency medical personnel with access to the sides of the patient's head, including the ears.

FIGS. 18A and 18B illustrate an alternative embodiment of a friction-based locking mechanism for holding a head block (105) in place on a base (115). By pushing down on a handle 1805 of a lock mechanism that is similar to lock mechanism 120 (shown in FIG. 6B), an internal lock feature of the lock mechanism causes a lock section 1810 to deflect out against base slot walls 1815 of base board 115 with sufficient normal pressure to hold head block 105 in place. The friction-based locking mechanism shown in FIGS. 18A and 18B is significantly simpler than lock mechanism 120 shown in FIG. 6B, thus simplifying a manufacturing process therefor.

Figure 19B:
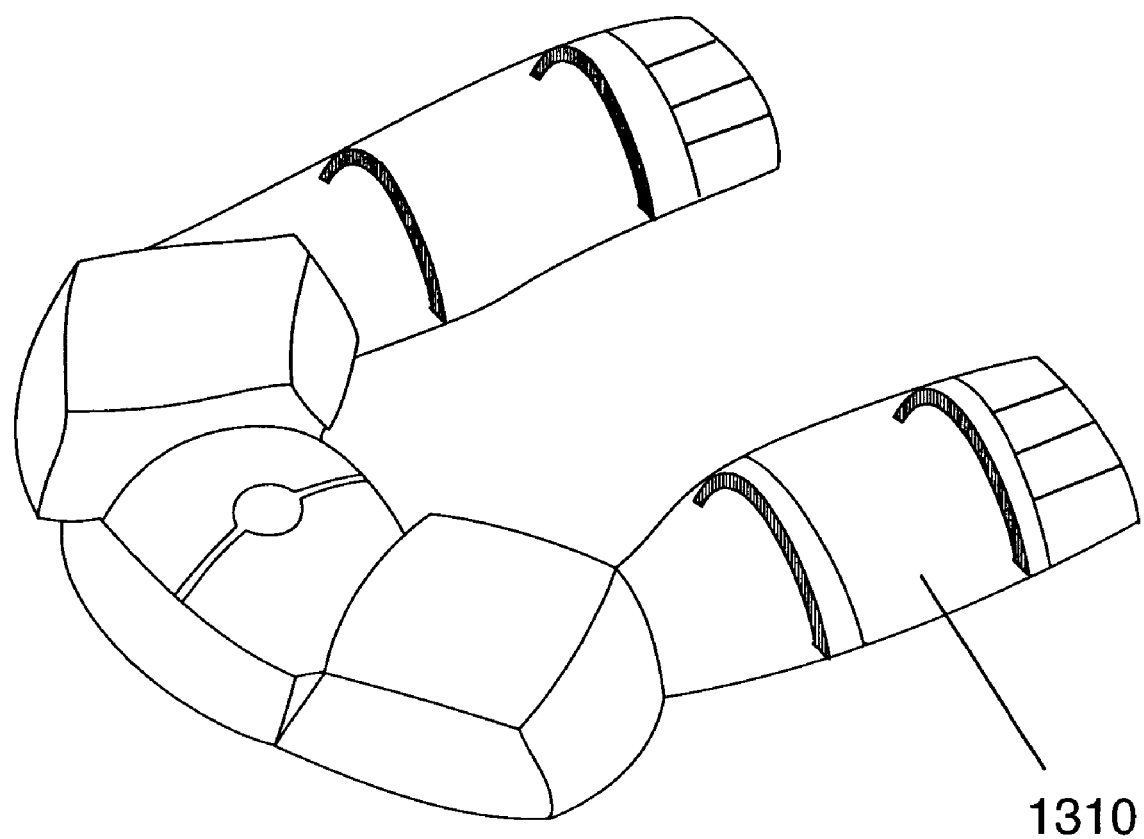
Figure 19C:
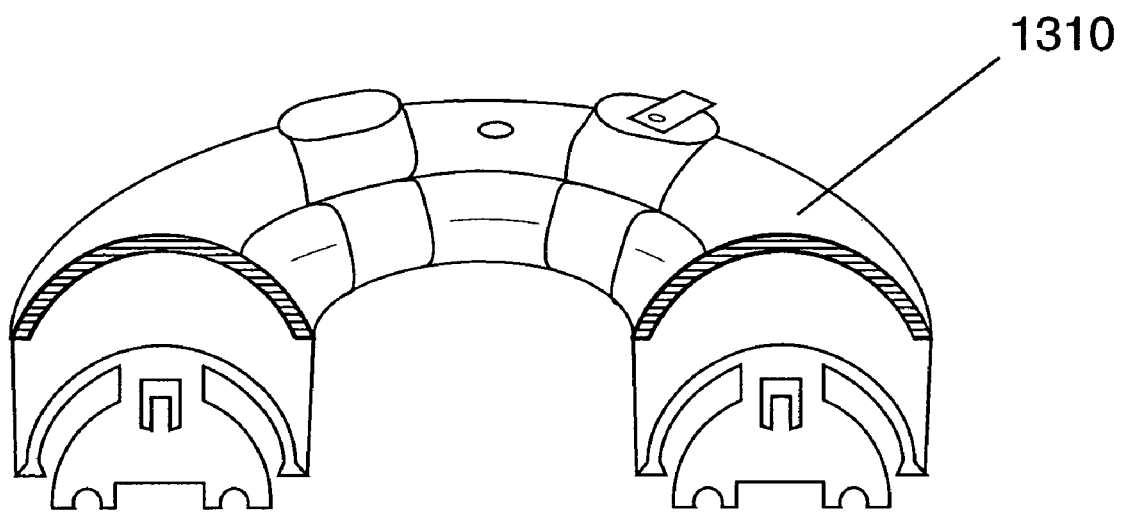

As described before, head blocks 105 and 110 may be taper-walled, having bell-shaped cross sections for minimizing x-ray artifacts. In further consideration of minimizing x-ray artifacts, head blocks 105 and 110 are preferably made from a relatively x-ray transparent material (and a disposable, cleanable, and rigid material)(e.g., a non-metallic material). FIGS. 19A, 19B, and 19C illustrate the x-ray transparent cross-sectional structure of upper portion 1310 (of head blocks 105 and 110) shown in FIGS. 13A, 13B, and 13C.

In order to provide sturdy head immobilization, head blocks 105 and 110 are preferably shaped so that they are sufficiently rigid. However, abrupt density (or thickness) changes of an object between an x-ray source and an image pickup, e.g., x-ray film or slide, causes x-ray artifacts. As shown in FIG. 19A, a curvilinear shape with tapered/feathered ends (or bell shape) causes significantly less x-ray artifacts than other rigid shapes, such as U-channel sections (with vertical walls) and ribbings. Therefore, as shown in FIGS. 19B and 19C, it is preferable that upper portion 1310 (of head blocks 105 and 110) have a cross section that is curvilinear with tapered/feathered ends (or bell shaped), and without any ribs or vertical walls.

As described before, arch openings 157 and 158 of head blocks 105 and 110 (as shown in FIG. 1) are provided so that the injured person's head, particularly the cervical spine area, is x-ray transparent. It is further noted that all fasteners (e.g., 140 and 155) and mechanisms (e.g., 120 and 125) for head blocks 105 and 110 are arranged away from the cervical spine area for similar reasons.

Figure 20A:
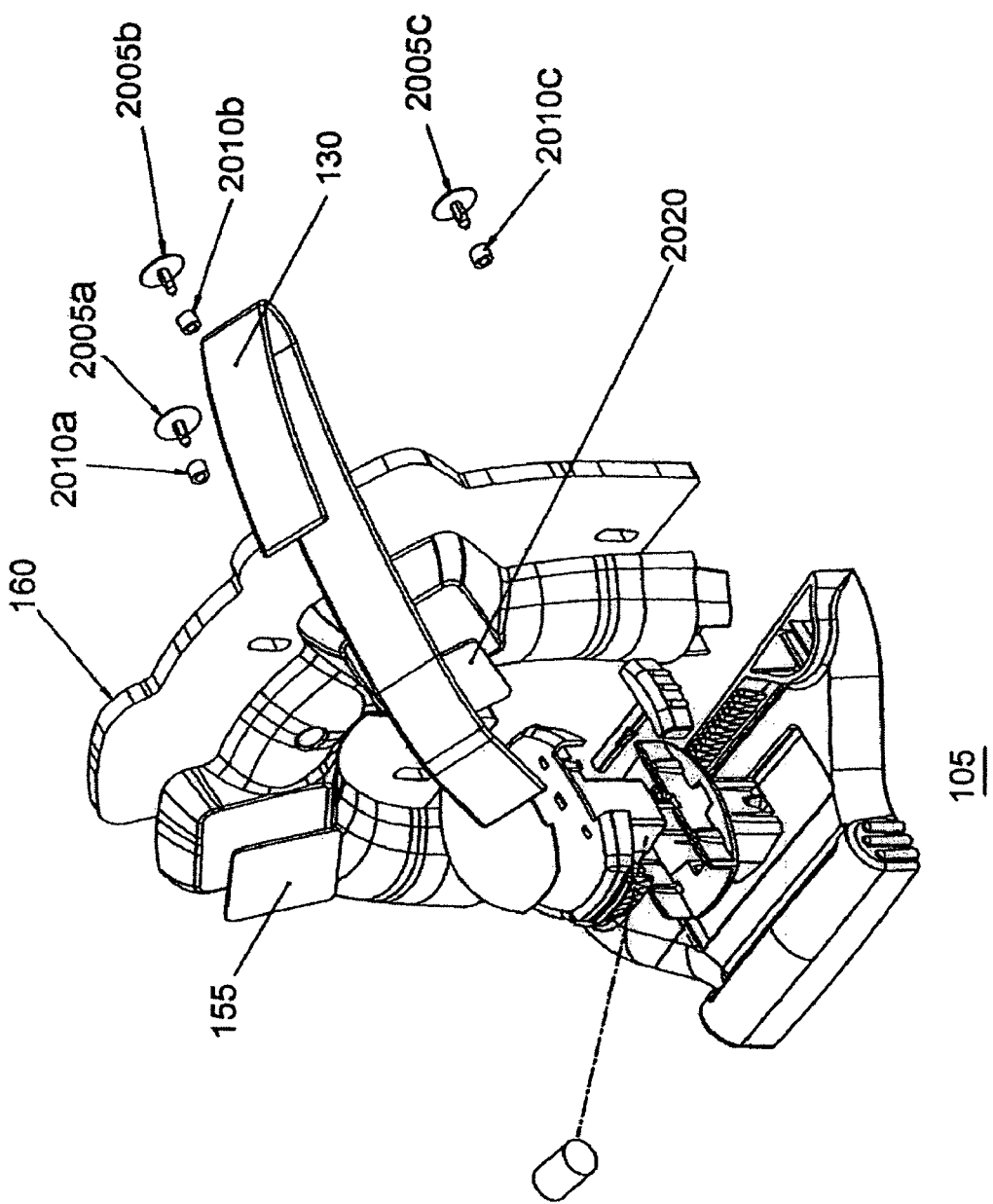

FIG. 20A is an exploded view of head block 105 in accordance with an embodiment of the invention. As shown in FIG. 20A, pad 160 may be removably attached to head block 105 by engaging rivets 2005a, 2005b and 2005c and washers 2010a, 2010b and 2010c to head block 105 through corresponding holes in pad 160. FIGS. 20B and 20C are diagrams illustrating holes 2015a, 2015b and 2015c on pad 160 for engaging rivets 2005a, 2005b and 2005c and washers 2010a, 2010b and 2010c. In accordance with an embodiment of the invention, head block 110 and pad 165 may include a similar structure, a description of which will not be repeated. As described before with reference to FIG. 1, pads 160 and 165 may be riveted to blocks 105 and 110 on their surfaces that come in contact with the patient. An additional pad 170 may be attached to headboard 115 to cushion the back of the head and to prevent sliding. FIG. 20D is a diagram illustrating the shape of additional pad 170 in accordance with an embodiment of the invention. Pads 160, 165, and 170 may be made with foam of a color dissimilar to the color of human blood and may be removably riveted or attached to head blocks 105 and 110 and headboard 115, respectively. Pads 160, 165, and 170 may also be fastened to head blocks 105 and 110 and headboard 115 by hook and loop fabric tape-style fasteners, two-sided adhesive fasteners, and the like. It is noted that any fasteners, such as buttons, additional straps, etc., may be used. Advantageously, a used pad (160, 165, or 170)—if contaminated from contact with a patient—may easily be identified and removed to be decontaminated and/or replaced without the need to replace entire head blocks 105 and 110 and headboard 115.

As further described with reference to FIG. 1, additional head motion restraint may be achieved by connecting strap 130, which may be attached to block 110 by rivet 135, to block 105 by releasable fastener 140 across the forehead of the injured person (see FIG. 11), and connecting a corresponding strap 145, which is attached to block 105 by a rivet 150, across the chin back to block 110 by a releasable fastener 155 (see FIG. 11). In accordance with the invention, rivets 135 and 150 and fasteners 140 and 155 may be rotatable or disposed at a predetermined angle so that straps 130 and 145 connected across the forehead and chin of the injured person may be angled to accommodate a wider range of head sizes. Referring back to FIG. 20A, rivet 135 may be replaced by a fastener 2020 similar to fastener 140. Correspondingly, rivet 150 (FIG. 1) may be replaced by a fastener (not shown) similar to fastener 155 (FIG. 1). In accordance with an embodiment of the invention, fasteners 140, 155 and 2020 may be hook and loop fabric tape-style fasteners that are attached to blocks 110 and 05, respectively, for fastening straps 130 and 145. Alternatively, the hook and loop fasteners could be removable or molded to the blocks to snap in and out. It is noted that any fasteners, such as buttons, two-sided adhesive fasteners, etc., may also be used. Advantageously, a used strap (130, 145) or fastener (140, 155 and 2020) may be removed to be decontaminated and/or replaced without the need to replace entire head blocks 105 and 110 and headboard 115.

In accordance with an embodiment of the invention, all elements, including straps (130 and 145), fasteners (140, 155 and 2020) and pads (160, 165, and 170), for contacting a patient's body part that is to be immobilized may be easily removed, decontaminated and/or replaced. These elements may also be packaged and sold as a kit of replaceable parts. For example, a kit may consist of two block pads, two head straps and one base pad. As a result, head blocks 105 and 110 and headboard 115 (or spine board 1400 as shown in FIG. 14) may be quickly reused by simply replacing the contact elements. Furthermore, head blocks 105 and 110 and headboard 115 (or spine board 1400 as shown in FIG. 14) may, thus, have an extended useful life for not having to be replaced for contamination of their respective contact elements. Thus, a replacement pad and strap kit for a head immobilization system may allow the durable components (such as head blocks 105 and 110 and headboard 115) to be reused indefinitely thereby reducing cleaning costs and minimizing exposure to pathogens. Such a kit of replaceable parts may also reduce material waste compared to having all disposable components without any durable components (i.e. head immobilizers). The durable components may be made of molded plastic material, which would make them essentially reusable but still low enough in cost to be disposed of when significantly contaminated.

Referring now to FIG. 21, replaceable parts in accordance with an embodiment of the present invention may also be used with a cervical (neck-stabilizing) collar. The collar comprises a neck band 2110, a mandible support 2160, and padding 2180. Padding 2180 is attached to the aforementioned components to enhance the comfort of the wearer. The padding 2180 consists of a piece of neck foam 2182 and a second piece of chin foam 2189. The neck foam 2182 has the same general shape as the neck band 2110 to which it is attached, but is sized to extend somewhat beyond the upper and lower margins of the neck band 2110. The foam is attached by a plurality of snaps, rivets, or other attachment structure provided for this purpose, and may be permanently or replacably attached to the neck band and mandible support. In the illustrated embodiment, the neck band 2110 is provided with a series of fastener holes for facilitating attachment of the neck pad via rivets. Similarly, chin foam 2189 is configured to overlie and provide padding for the chin piece 2130. As shown in FIG. 21, neck foam 2182 may be removably attached to neck band 2110 by engaging rivets 2190a, 2190b, 2190c, 2190d and 2190e and spacers 2191a, 2191b, 2191c, 2191d and 2191e to neck band 2110 through corresponding slots in neck foam 2182. Similarly, chin foam 2189 may be removably attached to chin piece 2160 by engaging spacers 2192a, 2192b and 2192c and rivets 2193a, 2193b and 2193c to chin piece 2130 through corresponding slots in chin foam 2189.

The neck band 2110 can be made from various stiff flexible plastics, including without limitation high and low density polyethylene, polyvinylchloride, acrylonitrile-butadiene-styrene copolymer, polypropylene, etc. Padding, straps and strips can be joined to the collar by any suitable fastening means, including without limitation snap fasteners, staples and adhesive. Although hook and loop fastening material is used as the preferred means to hold the collar in its neck encircling conformation, other means can be used to perform the same function, such as straps, buckles, snaps, fasteners, cords, tabbed strips or any other substantially non-stretch material with latching means. The cervical collar is further described in U.S. Pat. Nos. 5,795,315, 6,090,058 and Des. 393,718, which are hereby incorporated by reference.

Figure 22:
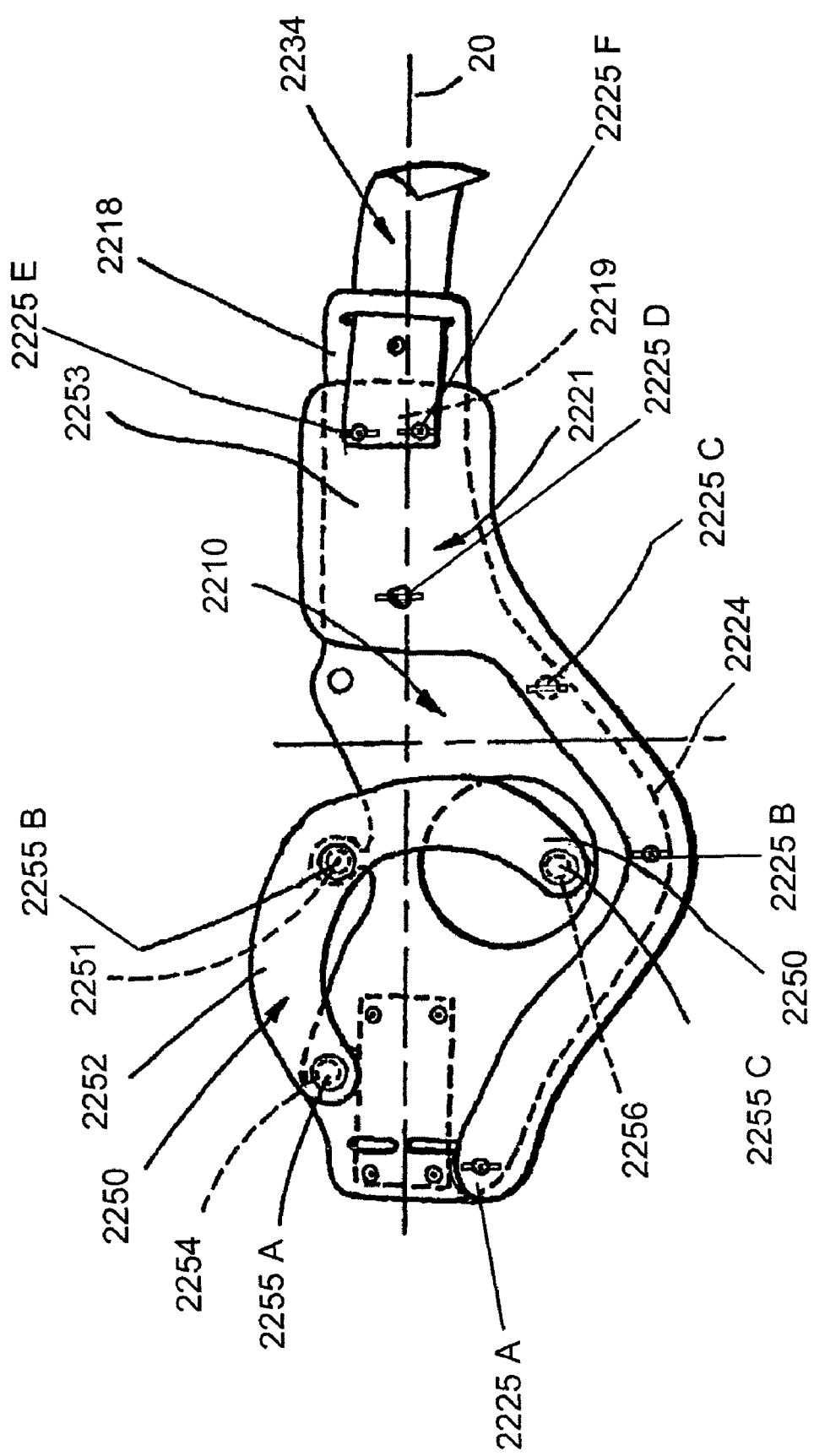
FIG. 22 illustrates a cervical collar in accordance with an embodiment of the invention in its flat, unassembled position.

FIG. 22 illustrates a cervical collar in accordance with another embodiment of the present invention. The collar comprises an elongated band 2210 which is formed of a stiff flexible sheet material such as various plastics, e.g., high and low density polyethylene, polyvinylchloride, acrylonitrile-butadiene-styrene copolymer, polypropylene, etc. A foam strip 2221 is preferably secured to the lower edge 2224 of the band 2210 by suitable fastening means, e.g., snap fasteners and/or staples. Cement or other bonding means can also be used. Preferably the foam strip 2221 includes a foam pad 2253 overlying the inside surface of back 2218, as shown. This provides additional comfort to the patient. The attachment band 2234 overlies a short portion 2219 of foam pad 2253. In accordance with an embodiment of the invention, attachment band 2234, and foam strip 2221 and/or foam pad 2253 may be removably attached to neck band 2210 by engaging rivets 2225*a*, 2225*b*, 2225*c*, 2225*d*, 2225*e*, and 2225*f* and corresponding spacers (not shown) to neck band 2210 through corresponding slots in attachment band 2234, and foam strip 2221 and/or foam pad 2253. Alternatively, instead of securing the neck band 2210 over the rivets, hooks (not shown) could be provided at both ends of the neck band 2210 to removably attach the foam strip 2221 and/or foam pad 2253 to the neck band 2210. Similarly, the entire inside surface of the chin support brace 2250 can receive a cushioning (foam) pad. The pads which are used can be foamed plastics such as polyethylene and polyurethane. Most preferably, the foam strip projects a slight distance past the lower edge 2224, as shown to provide maximum cushioning to the patient. The chin support brace 2250 is a generally C-shaped plate 2252 which has distal apertures 2254 and 2256 and a central aperture 2251. A cushioning (foam) pad may removably attached to chin support brace (C-shaped plate 2252) by engaging rivets 2255*a*, 2255*b*, and 2255*c* and corresponding washers (not shown) through apertures 2251, 2254 and 2256 and corresponding apertures in the cushioning pad. Other features of the cervical collar of FIG. 22 are further described in U.S. Pat. Nos. 4,413,619 and Re. 32,219, which are hereby incorporated by reference.

Thus, a replacement pad and strap kit for a cervical collar (e.g., neck band 2110 or neck band 2210) may allow the durable components to be reused indefinitely thereby reducing costs and minimizing exposure to pathogens. Such a kit of replaceable parts may also reduce material waste compared to having all disposable components without any durable components.

It will thus be seen that the objects set forth above, among those made apparent from the preceding description, are efficiently attained and, because certain changes may be made in carrying out the above method(s) and in the construction(s) set forth without departing from the spirit and scope of the invention, it is intended that all matter contained in the above description and shown in the accompanying drawings shall be interpreted as illustrative and not in a limiting sense. For example, the described embodiments apply to immobilizing an injured person's head. However, the invention may be applied to immobilizing other parts of the body, such as an injured person's knee, pelvis, etc.

It is also to be understood that the following claims are intended to cover all of the generic and specific features of the invention herein described and all statements of the scope of the invention which, as a matter of language, might be said to fall therebetween.

What is claimed is:

1. A body part immobilization apparatus, comprising:
   one or more side blocks for securing at least one side of a body part, the one or more side blocks having respective positional engagement means and a bell shape with an arched opening;
   a base for mounting the one or more side blocks, said base having adjustable engagement means; and
   respective attachment means for adjustably attaching each of the one or more side blocks to the base by engaging the adjustable engagement means and the respective positional engagement means,
   wherein the one or more side blocks comprises a body part contact means removably attached thereto for contacting the body part and wherein the body part contact means has a bell shape with an arched opening.

2. The body part immobilization apparatus of claim 1, wherein said body part contact means comprises a foam pad.

3. The body part immobilization apparatus of claim 1, wherein said body part contact means comprises a hook and loop fabric type-style fastener.

4. The body part immobilization apparatus of claim 1 wherein said body part contact means has a shape which substantially corresponds to the shape of a mating face of said side block to which said body part contact means is removably attached.

5. The body part immobilization apparatus of claim 1 wherein said body part contact means is of a color which is dissimilar to the color of said side block to which said body part contact means is removably attached.

6. The body part immobilization apparatus of claim 1 wherein said body part contact means is removably attached to said corresponding side block by means of a two-sided adhesive fastener.

7. The body part immobilization apparatus of claim 1 wherein said body part contact means allows for re-use of said corresponding side block.

8. The body part immobilization apparatus of claim 1 wherein the one or more side blocks further comprise strap fastening means removably attached thereto for removably fastening a restraining strap extending across a body part.

9. The body part immobilization apparatus of claim 8 wherein the strap fastening means is rotatable so that a surface of the extended strap is adjustable to a particular angle.

10. The body part immobilization apparatus of claim 8 wherein said strap fastening means comprises a hook and loop fabric type-style fastener.

11. The body part immobilization apparatus of claim 8 wherein the strap fastening means is disposed at a particular angle so that a surface of the extended strap is at said angle.

12. The body part immobilization apparatus of claim 8 wherein said body part contact means and said strap are capable of being easily removed, decontaminated and replaced.

13. The body part immobilization apparatus of claim 1 wherein said body part contact means are removably attached to the corresponding side block by extending fastening means through corresponding openings in said body part contact means to engage said corresponding side block.

14. A body part immobilization apparatus, comprising:
   one or more side blocks for securing at least one side of a body part, the one or more side blocks having respective positional engagement means;
   a base for mounting the one or more side blocks, said base having adjustable engagement means;

a plunger-type lock for adjustably attaching each of the one or more side blocks to the base by engaging at least one of the adjustable engagement means and the respective positional engagement means by depressing the plunger-type lock.

15. The body part immobilization apparatus of claim 14, wherein the respective positional engagement means and the adjustable engagement means each comprise an elongated slot and wherein the plunger-type lock comprises means for engaging at least one of the elongated slots.

16. The body part immobilization apparatus of claim 15, wherein at least one of the elongated slots comprises a plurality of teeth, and wherein the plunger-type lock comprises a flexible finger that engages at least one of the plurality of teeth in the elongated slot having the plurality of teeth.

17. The body part immobilization apparatus of claim 14, wherein the respective positional engagement means and the adjustable engagement means each comprise an elongated slot, at least one of the elongated slots comprising a rack, and wherein the plunger-type lock comprises a flexible finger that engages the rack in the elongated slot having the rack.

18. The body part immobilization apparatus of claim 17, wherein the flexible finger comprises a tooth that engages the rack in the elongated slot having the rack.

19. The body part immobilization apparatus of claim 14, wherein one or more of the side blocks comprises a plurality of teeth and wherein the plunger-type lock comprises at least one corresponding tooth that engages one or more of the plurality of teeth of the side block when the plunger-type lock is depressed.

20. The body part immobilization apparatus of claim 14, wherein the plunger-type lock comprises means for disengaging the lock from at least one of the adjustable engagement means and the respective positional engagement means.

21. The body part immobilization apparatus of claim 14, wherein the plunger-type lock adjustably attaches one or more of the side blocks to the base in a first stage and a second stage, in the first stage the plunger-type lock restricts movement in a vertical plane and in the second stage the plunger-type lock restricts movement in at least one of longitudinally and laterally by further depressing the plunger-type lock when in the first stage.

22. The body part immobilization apparatus of claim 14, wherein the one or more side block comprises a body part contact means removably attached thereto for contacting the body part.

23. A body part immobilization apparatus, comprising:
one or more side blocks for securing at least one side of a body part, the one or more side blocks having respective positional engagement means;
a base for mounting the one or more side blocks, said base having adjustable engagement means; and
a plunger-type lock for adjustably attaching each of the one or more side blocks to the base by engaging at least one of the adjustable engagement means and the respective positional engagement means, wherein the plunger-type lock adjustably attaches one or more of the side blocks to the base in a first stage and a second stage, in the first stage the plunger-type lock restricts movement of the one or more side blocks in a vertical plane and in the second stage the plunger-type lock restricts movement of the one or more side blocks in at least one of longitudinally and laterally by further depressing the plunger-type lock when in the first stage.

24. A body part immobilization apparatus, comprising:
one or more side blocks for securing at least one side of a body part, the one or more side blocks having an elongated slot disposed therein;
a base for mounting the one or more side blocks, said base having an elongated slot disposed therein; and
a plunger-type lock for adjustably attaching each of the one or more side blocks to the base by engaging at least one of the elongated slots, wherein at least one of the elongated slots comprises a rack and wherein the plunger-type lock comprises a flexible finger that engages the rack in the elongated slot having the rack by depressing the plunger-type lock to restrict vertical movement.

25. A body part immobilization apparatus, comprising:
one or more side blocks for securing at least one side of a body part;
a base for mounting the one or more side blocks; and
a plunger-type lock for adjustably attaching each of the one or more side blocks to the base, wherein one or more of the side blocks comprises a plurality of teeth and wherein the plunger-type lock comprises at least one corresponding tooth that engages one or more of the plurality of teeth of the side block when the plunger-type lock is depressed.

26. A body part immobilization apparatus, comprising:
one or more side blocks for securing at least one side of a body part, the one or more side blocks having respective positional engagement means and a bell shape with an arched opening;
a base for mounting the one or more side blocks, said base having adjustable engagement means; and
plunger-type lock for adjustably attaching each of the one or more side blocks to the base by engaging at least one of the adjustable engagement means and the respective positional engagement means,
wherein the one or more side blocks comprises a body part contact means having an outer bell shape with an arched opening removably attached to the side block for contacting the body part, the arched opening comprising at least at least one curved portion, and the outer bell shape having a plurality of projections extending therefrom essentially symmetrical about a vertical axis.

* * * * *